US010960069B2

(12) United States Patent
Li et al.

(10) Patent No.: US 10,960,069 B2
(45) Date of Patent: Mar. 30, 2021

(54) DEVELOPMENT OF A PREVENTIVE INFLUENZA D VIRUS VACCINE

(71) Applicant: The Board of Regents of the University of Nebraska, Lincoln, NE (US)

(72) Inventors: Qingsheng Li, Lincoln, NE (US); Yanmin Wan, Lincoln, NE (US); Feng Li, Brookings, SD (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 16/353,626

(22) Filed: Mar. 14, 2019

(65) Prior Publication Data

US 2019/0282687 A1  Sep. 19, 2019

Related U.S. Application Data

(60) Provisional application No. 62/642,861, filed on Mar. 14, 2018.

(51) Int. Cl.
| *A61K 39/00* | (2006.01) |
|---|---|
| *A61K 39/12* | (2006.01) |
| *A61K 39/21* | (2006.01) |
| *C07K 14/00* | (2006.01) |
| *A61K 38/16* | (2006.01) |
| *A61K 39/145* | (2006.01) |
| *A61K 9/00* | (2006.01) |
| *A61P 31/16* | (2006.01) |
| *C12N 9/18* | (2006.01) |
| *C12N 7/00* | (2006.01) |

(52) U.S. Cl.
CPC .......... *A61K 39/145* (2013.01); *A61K 9/0019* (2013.01); *A61K 9/0043* (2013.01); *A61K 9/0053* (2013.01); *A61P 31/16* (2018.01); *C12N 7/00* (2013.01); *C12N 9/18* (2013.01); *C12Y 301/01053* (2013.01); *A61K 2039/54* (2013.01); *A61K 2039/545* (2013.01); *A61K 2039/552* (2013.01); *A61K 2039/70* (2013.01); *C07K 2319/00* (2013.01); *C12N 2760/16034* (2013.01); *C12N 2760/16071* (2013.01)

(58) Field of Classification Search
CPC .......... C12N 15/86; C12N 2740/15043; A61K 2039/5252; A61K 2039/5254; A61K 2039/552

See application file for complete search history.

(56) References Cited

FOREIGN PATENT DOCUMENTS

WO   WO2017087492   *   5/2017

* cited by examiner

*Primary Examiner* — Barry A Chestnut
(74) *Attorney, Agent, or Firm* — Tracey S. Truitt; Armstrong Teasdale LLP

(57) ABSTRACT

The present disclosure provides a DNA vaccine or immunogenic composition expressing consensus hemagglutinin-esterase-fusion (HEF) protein (FluD-Vax) and a protein-based vaccine utilizing the HEF consensus protein. Methods of making and using the compositions are also provided herein.

20 Claims, 7 Drawing Sheets
Specification includes a Sequence Listing.

FIG. 4A | FIG. 4B | FIG. 4C
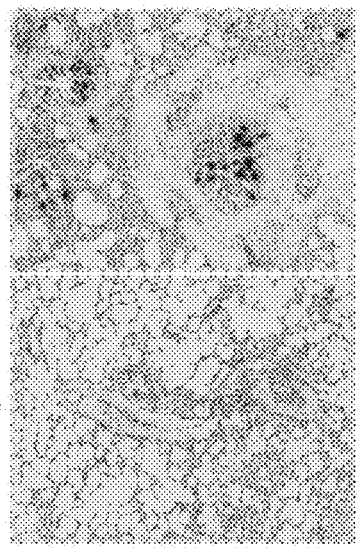 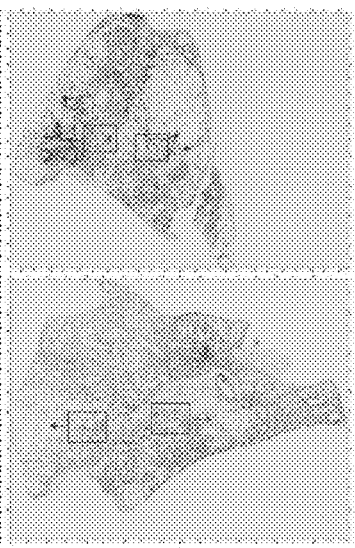 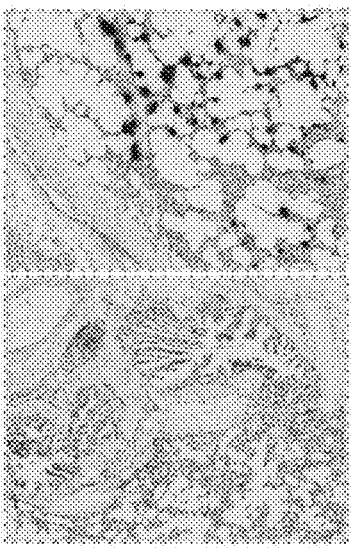
FIG. 4D | FIG. 4E | FIG. 4F
IDV D/OK Intranasal Challenge
FIG. 4G | FIG. 4H | FIG. 4I
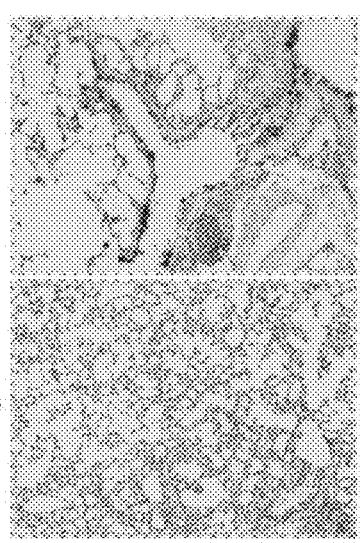 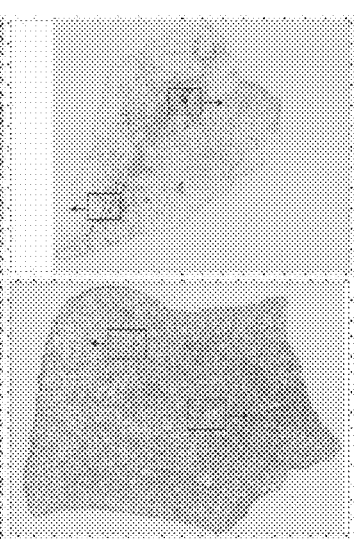 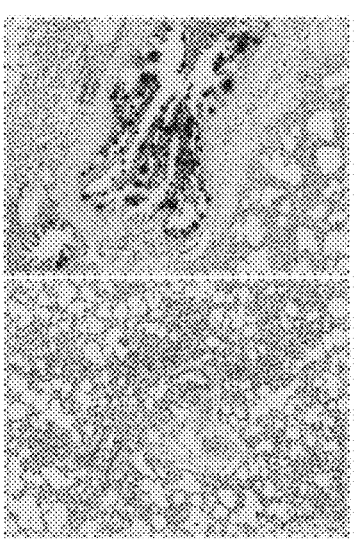
FIG. 4J | FIG. 4K | FIG. 4L
IDV D/660 Intranasal Challenge FIG. 6A
FIG. 6B
FIG. 6C
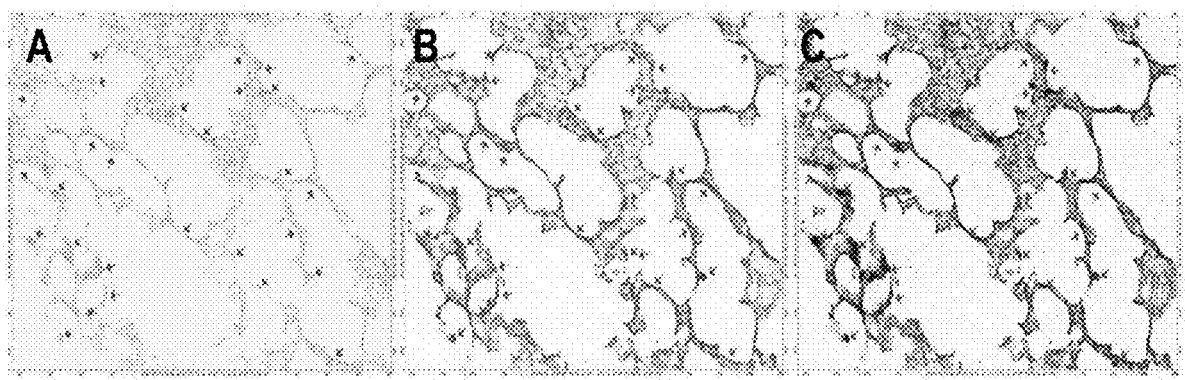
FIG. 6D
FIG. 6E
FIG. 6F
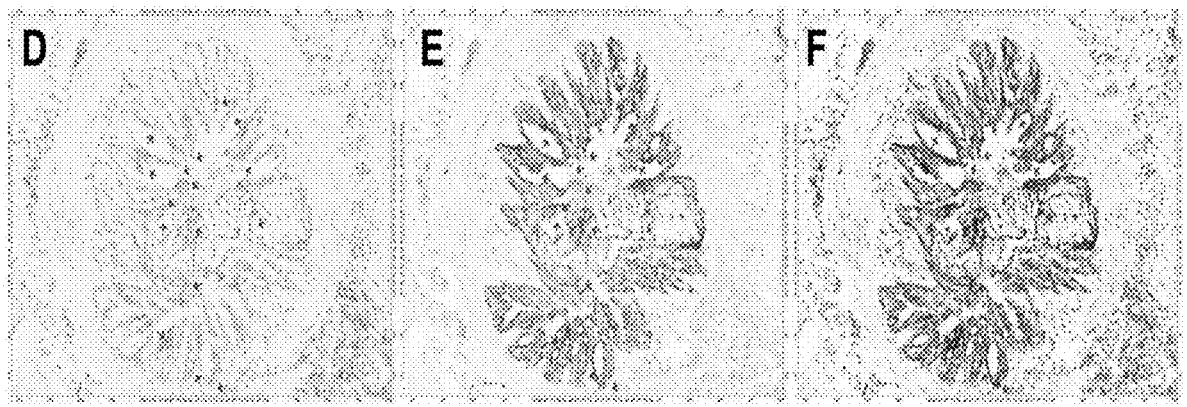

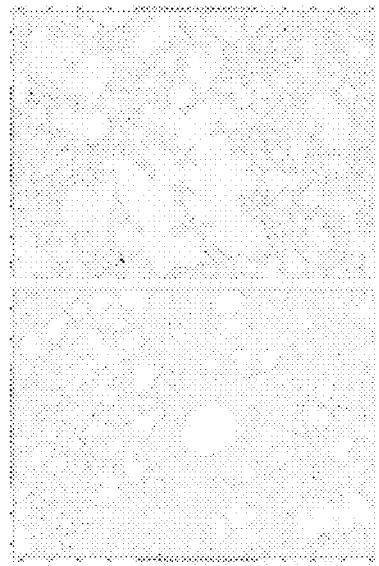
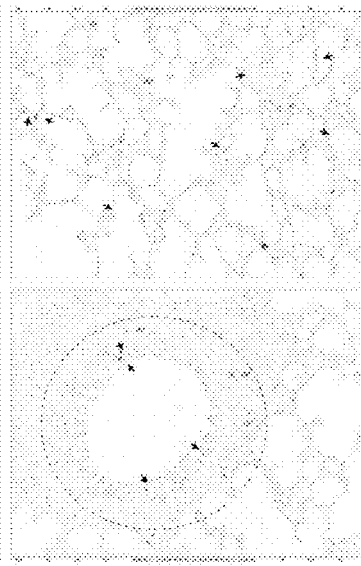
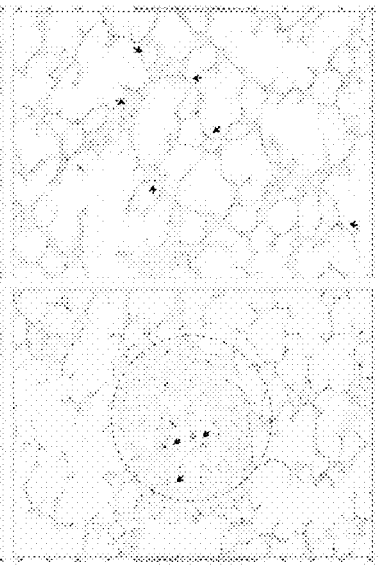
FIG. 7A  FIG. 7B  FIG. 7C
FIG. 7D  FIG. 7E  FIG. 7F
FIG. 7G  FIG. 7H  FIG. 7I
FIG. 7J  FIG. 7K  FIG. 7L
TUNEL-Positive: IDV D/660 Challenge
TUNEL-Positive: IDV D/660 Challenge

DEVELOPMENT OF A PREVENTIVE INFLUENZA D VIRUS VACCINE

STATEMENT REGARDING FEDERALLY SPONSORED RESEARCH OR DEVELOPMENT

None.

BACKGROUND

Influenza D virus (IDV) has recently been classified as a new genus within the Orthomyxoviridae family and is distinct from influenza A, B, and C viruses (IAV, IBV, ICV, respectively). IDV infects economically important domestic livestock, including swine and cattle, and has been associated with a respiratory disease/influenza-like illness. Furthermore, IDV seroprevalence in humans was estimated to be approximately 1.3% in the general population and over 90% in individuals working with cattle. These initial studies suggest that IDV may have the potential to infect humans, although its pathogenicity to humans remains unknown.

IDV has a broad host range. IDV was initially isolated from clinically ill pigs expressing influenza-like symptoms in 2011. However, subsequently epidemiological data suggest cattle are the primary reservoir. In addition to swine and cattle, IDV infections have been reported in goat, sheep, equine, buffalo, and camel. IDV has also been shown to infect ferrets and guinea pigs in experimental settings. IDV infections are widely distributed across many countries in the American, Asian, European, and African continents. With a broad host range and high environmental stability, IDV has the potential to further gain virulence, or even infect humans.

Two lineages of IDVs were found to be co-circulating in the United States. Recently, a potential third lineage of IDV was identified in Japan. IDV, like other Influenza viruses, is a single-strand, negative-sense segmented and enveloped RNA virus. Both IAV and IBV have eight genomic segments and two surface glycoproteins of hemagglutinin (HA) and neuraminidase (NA). IDV like ICV has only seven genomic segments and one spike hemagglutinin-esterase-fusion (HEF) protein. The HEF combines the functions of HA and NA for receptor binding, receptor destruction, and membrane fusion activity. While the overall structure of IDV HEF is similar to ICV, IDV HEF has an open receptor binding cavity to accommodate diverse extended glycan moieties, which may be one of the reasons for its broad host range.

IDV causes only mild or no obvious clinical symptoms in infected animals. However, it is thought to be a facilitating factor for the development of bovine respiratory disease complex (BRDC), which is one of the most commonly diagnosed causes of morbidity and mortality within the cattle industry. An efficacious preventative vaccine is needed to protect economically important domestic animals and limit potential cross-species transmission to humans.

What is needed is an immunogenic composition that provides protection against IDV infection and/or reduces at least one of the following: the incidence of IDV infection, the severity of clinical signs caused by or associated with IDV infection, the incidence of clinical signs caused by or associated with IDV infection, and the susceptibility to IDV infection. What is further needed is an immunogenic composition that reduces the possibility of cross-species transmission of IDV to other animals including humans.

SUMMARY OF THE DISCLOSURE

The present disclosure overcomes the problems inherent in the art including those described above.

IDV infection has been associated with BRDC, one of the most devastating diseases of the cattle population. An efficacious vaccine is needed to prevent infection and stop potential cross-species transmission. In this study, a DNA vaccine encoding the consensus HEF of two lineages of IDV (D/OK and D/660) (SEQ ID NO. 1) was designed and its efficacy was tested in a guinea pig model. The results showed that the consensus DNA vaccine (SEQ ID NO. 2) elicited high-titer neutralizing antibodies and achieved sterilizing protection against two lineage-representative IDV intra-nasal infections. It is believed that this is the first study showing a DNA vaccine-expressing consensus HEF is efficacious in preventing different lineages of influenza D virus infections.

In one aspect of the disclosure, a DNA vaccine or immunogenic composition is provided. Preferably, the vaccine or immunogenic composition has a nucleotide sequence having at least 85%, more preferably 90%, still more preferably 91, 92, 93, 94, 95, 96, 97, 98, 99, 99.5, or 100% sequence homology with SEQ ID NO. 2 and/or encodes an amino acid sequence having at least 85%, more preferably 90%, still more preferably 91, 92, 93, 94, 95, 96, 97, 98, 99, 99.5, or 100% sequence homology with SEQ ID NO. 1.

In another aspect of the disclosure, a protein-based vaccine or immunogenic composition is provided. Preferably, the vaccine or immunogenic composition is encoded by a nucleotide sequence having at least 85%, more preferably 90%, still more preferably 91, 92, 93, 94, 95, 96, 97, 98, 99, 99.5, or 100% sequence homology with SEQ ID NO. 2 and/or has an amino acid sequence having at least 85%, more preferably 90%, still more preferably 91, 92, 93, 94, 95, 96, 97, 98, 99, 99.5, or 100% sequence homology with SEQ ID NO. 1.

In another aspect of the disclosure, a method of reducing the incidence of or severity of clinical signs of IDV infection in an individual animal is provided. In general, the method comprises the step of administering an immunogenic composition or vaccine to an animal in need thereof wherein the immunogenic composition has a nucleotide sequence having at least 85%, more preferably 90%, still more preferably 91, 92, 93, 94, 95, 96, 97, 98, 99, 99.5, or 100% sequence homology with SEQ ID NO. 2 and/or encodes an amino acid sequence having at least 85%, more preferably 90%, still more preferably 91, 92, 93, 94, 95, 96, 97, 98, 99, 99.5, or 100% sequence homology with SEQ ID NO. 1. In some forms, the nucleotide sequence is combined with a carrier. In some forms, the nucleotide sequence is combined with an adjuvant. In some forms, the nucleotide sequence is contained within a vector. In some forms, the vector is a plasmid. In some forms, the vector is the pJW4303 vector.

In another aspect of the disclosure, a method of reducing the incidence of or severity of clinical signs of IDV infection in a group or herd of animals is provided. In general, the method comprises the step of administering an immunogenic composition or vaccine to a group of animals in need thereof wherein the immunogenic composition has a nucleotide sequence having at least 85%, more preferably 90%, still more preferably 91, 92, 93, 94, 95, 96, 97, 98, 99, 99.5, or 100% sequence homology with SEQ ID NO. 2 and/or encodes an amino acid sequence having at least 85%, more preferably 90%, still more preferably 91, 92, 93, 94, 95, 96, 97, 98, 99, 99.5, or 100% sequence homology with SEQ ID NO. 1. In some forms, the nucleotide sequence is combined with a carrier. In some forms, the nucleotide sequence is combined with an adjuvant. In some forms, the nucleotide sequence is contained within a vector. In some forms, the vector is a plasmid. In some forms, the vector is the pJW4303 vector.

In another aspect of the disclosure, a method of reducing the incidence of or severity of clinical signs of IDV infection in an individual animal is provided. In general, the method comprises the step of administering an immunogenic composition or vaccine to an animal in need thereof wherein the immunogenic composition is encoded by a nucleotide sequence having at least 85%, more preferably 90%, still more preferably 91, 92, 93, 94, 95, 96, 97, 98, 99, 99.5, or 100% sequence homology with SEQ ID NO. 2 and/or has an amino acid sequence having at least 85%, more preferably 90%, still more preferably 91, 92, 93, 94, 95, 96, 97, 98, 99, 99.5, or 100% sequence homology with SEQ ID NO. 1. In some forms, the amino acid sequence is combined with a carrier. In some forms, the amino acid sequence is combined with an adjuvant.

In another aspect of the disclosure, a method of reducing the incidence of or severity of clinical signs of IDV infection in a group or herd of animals is provided. In general, the method comprises the step of administering an immunogenic composition or vaccine to a group of animals in need thereof wherein the immunogenic composition is encoded by a nucleotide sequence having at least 85%, more preferably 90%, still more preferably 91, 92, 93, 94, 95, 96, 97, 98, 99, 99.5, or 100% sequence homology with SEQ ID NO. 2 and/or has an amino acid sequence having at least 85%, more preferably 90%, still more preferably 91, 92, 93, 94, 95, 96, 97, 98, 99, 99.5, or 100% sequence homology with SEQ ID NO. 1. In some forms, the amino acid sequence is combined with a carrier. In some forms, the amino acid sequence is combined with an adjuvant.

In another aspect of the disclosure, a method of making an immunogenic composition or vaccine that provides protection by reducing the incidence of or severity of clinical signs of IDV infection in an individual animal or group of animals is provided. The method generally comprises the steps of inserting a desired nucleotide sequence into a vector and administering the vector to an animal or animals in need thereof. Preferably, the nucleotide sequence has at least 85%, more preferably 90%, still more preferably 91, 92, 93, 94, 95, 96, 97, 98, 99, 99.5, or 100% sequence homology with SEQ ID NO. 2 and/or encodes an amino acid sequence having at least 85%, more preferably 90%, still more preferably 91, 92, 93, 94, 95, 96, 97, 98, 99, 99.5, or 100% sequence homology with SEQ ID NO. 1. In some forms, the vector containing the nucleotide sequence is combined with a carrier. In some forms, the vector containing the nucleotide sequence is combined with an adjuvant. In some forms, the vector is a plasmid. In some forms, the vector is the pJW4303 vector. Preferably, the inserted nucleotide sequence is expressed in vivo after being administered to the animal or group of animals.

In another aspect of the disclosure, a method of making an immunogenic composition or vaccine is provided. The method generally includes the step of recovering an expressed protein or constructing a recombinant protein and using that protein as the immunogenic composition or vaccine. In some forms, the protein is expressed by a nucleotide sequence having at least 85%, more preferably 90%, still more preferably 91, 92, 93, 94, 95, 96, 97, 98, 99, 99.5, or 100% sequence homology with SEQ ID NO. 2. In some forms, the expressed protein or constructed recombinant protein has an amino acid sequence having at least 85%, more preferably 90%, still more preferably 91, 92, 93, 94, 95, 96, 97, 98, 99, 99.5, or 100% sequence homology with SEQ ID NO. 1. In some forms, the amino acid sequence is combined with a carrier. In some forms, the amino acid sequence is combined with an adjuvant. In some forms, the nucleotide sequence used to express the amino acid sequence is contained within a vector. In some forms, the vector is a plasmid. In some forms, the vector is the pJW4303 vector.

In another aspect of the disclosure, the immunogenic composition or vaccine as disclosed herein is combined with or administered concurrently with an antigen that reduces the incidence of or severity of clinical signs of another pathogen. In some forms, the other pathogen is a virus. In some forms, the other pathogen is a bacteria. In some forms, the immunogenic composition of the present disclosure is combined with the other antigen such that they are in the same container or administration vehicle. In some forms, the other antigen is administered concurrently or within 5 minutes, 1 hour, 3 hours, 5 hours, 10 hours, 18 hours, 24 hours, 36 hours, 48 hours, 72 hours, or 96 hours of the administration of the immunogenic composition or vaccine of the present disclosure. In some forms, the pathogen is selected from the group consisting of at least one swine pathogen, preferably one described below and/or at least one cattle pathogen, preferably selected from the group consisting of Bovine Viral Diarrhea Virus, Bovine Herpesvirus, Pasteurella, Mannheimia, Bluetongue Virus, Bovine Parvovirus, Bovine Parainfluenza Virus, Bovine Respiratory Syncytial Virus, and Fusobacterium.

In another aspect of the disclosure a method of producing and/or recovering recombinant HEF IDV protein is provided. In general, the method includes the steps of 1) infecting a number of susceptible cells in culture with a recombinant viral vector encoding a HEF IDV protein, 2) expressing HEF IDV protein by the recombinant viral vector, 3) recovering the HEF IDV protein, and, 4) separating cell debris from the expressed HEF IDV protein via a separation step.

In another aspect of the present disclosure, the inclusion of an inactivation step is preferred in order to inactivate the viral vector prior to recovery of HEF IDV protein that will be used in an immunogenic or immunological composition such as a vaccine. Such a step can be performed as step 5) in addition to steps 1-4 described above.

In some forms, this inactivation is done either just before or just after the filtration or separation step. Any conventional inactivation method can be used for purposes of the present disclosure. Thus, inactivation can be performed by chemical and/or physical treatments. One representative inactivation method includes the addition of cyclized binary ethylenimine (BEI).

Optionally, the method described above may also include a neutralization step after step 5). For example, if the inactivation agent is BEI, addition of sodium thiosulfate to an equivalent amount is preferred. Preferably, the sodium thiosulfate is added in equivalent amount as compared to the BEI added for inactivation.

An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction in the severity or prevalence of, up to and including a lack of symptoms normally displayed by an infected host, a quicker recovery time and/or a lowered viral titer in the infected host.

In preferred forms and especially in forms that will use the recombinant HEF IDV protein in an immunogenic composition such as a vaccine, each lot or just selected lots of harvested HEF IDV protein can be tested for inactivation. Thus a further aspect of the present disclosure relates to an inactivation test for determining the effectiveness of the inactivation of the recombination viral vector, comprising the steps: 1) contacting at least a portion of the culture fluid containing the recombinant viral vector with an inactivating agent, 2) adding a neutralization agent to neutralize the inactivation agent, and 3) determining the residual infectivity.

In preferred forms the recombinant viral vector containing HEF IDV DNA and expressing HEF IDV protein used to infect the cells is generated by transfecting a transfer vector that has had a HEF IDV gene cloned therein into a viral vector. Preferably, only the portion of the transfer vector that contains the desired HEF IDV DNA is transfected into the viral vector.

The term "transfected into a viral vector" means, and is used as a synonym for "introducing" or "cloning" a heterologous DNA into a viral vector, such as for example into a baculovirus vector. A "transfer vector" means a DNA molecule, that includes at least one origin of replication, the heterologous gene, in the present case of HEF IDV, DNA sequences which allow the cloning of said heterologous gene into the viral vector will be included. Preferably the sequences which allow cloning of the heterologous gene into the viral vector are flanking the heterologous gene. Even more preferably, those flanking sequences are at least homologous in parts with sequences of the viral vector. The sequence homology then allows recombination of both molecules, the viral vector, and the transfer vector to generate a recombinant viral vector containing the heterologous gene.

In another aspect of the disclosure, a method of making the HEF IDV protein will begin with the isolation of HEF IDV DNA. Any HEF IDV gene can be used for purposes of the present disclosure. The HEF IDV DNA is preferably amplified using PCR methods. The resulting DNA is then cloned into the transfer vector.

Thus, in one aspect of the present disclosure, a method for constructing a recombinant viral vector containing HEF IDV DNA is provided. This method generally comprises the steps of: 1) cloning at least one recombinant HEF IDV gene into a transfer vector;

and 2) transfecting the portion of the transfer vector containing the recombinant HEF IDV gene into a viral vector, to generate the recombinant viral vector.

A further aspect of the present disclosure relates to a method for preparing a composition comprising HEF IDV protein, and inactivated viral vector. This method generally comprises the steps of: 1) cloning the amplified HEF IDV DNA into a transfer vector; 2) transfecting the portion of the transfer vector containing the recombinant HEF IDV DNA into a virus; 3) infecting cells in media with the transfected viral vector; 4) causing the transfected viral vector to express the recombinant protein from the HEF IDV DNA; 5) separating cells from the supernate; 6) recovering the expressed HEF IDV protein; and 7) inactivating the recombinant viral vector. In preferred forms and as described above, a neutralization step, step 8), will be performed after step 7). Of course, prior to step 1) the HEF IDV DNA can be amplified in vitro, preferably with flanking sequences of the HEF IDV DNA, as described above.

In another aspect of the present disclosure, a method for preparing a composition, preferably an immunogenic composition, such as a vaccine, for invoking an immune response against HEF IDV is provided. Generally, this method includes the steps of transfecting a construct into a virus, wherein the construct comprises 1) recombinant DNA from HEF IDV, 2) infecting cells in growth media with the transfected virus, 3) causing the virus to express the recombinant protein from HEF IDV, 4) recovering the expressed recombinant protein, 5) and preparing the composition by combining the recovered protein with a suitable adjuvant and/or other pharmaceutically acceptable carrier. In some preferred forms, the composition also includes at least a portion of the viral vector expressing said HEF IDV protein, and/or a portion of the cell culture supernate "Adjuvants" as used herein, can include aluminum hydroxide and aluminum phosphate, saponins e.g., Quil A, QS-21 (Cambridge Biotech Inc., Cambridge, Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups.

The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta, Ga.), SAF-M (Chiron, Emeryville, Calif.), monophosphoryl lipid A, Avridine lipid-amine adjuvant, heat-labile enterotoxin from *E. coli* (recombinant or otherwise), cholera toxin, IMS 1314 or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

In another aspect of the present disclosure, a method for preparing an immunogenic composition, such as a vaccine, for invoking an immune response against HEF IDV comprises the steps of 1) expressing and recovering HEF IDV protein, and 2) admixing the recovered protein with a suitable adjuvant. Preferably, the expressing step 1) includes the steps as described for the preparation and recovery of HEF IDV protein. Another optional step for this method includes cloning the amplified HEF IDV DNA into a first vector, excising the DNA from this first vector, and using this excised HEF IDV DNA for cloning into the transfer vector. Preferably, the recovery step of this method also includes the step of separating the media from the cells and cell debris. This can be done in any conventional manner, with one preferred manner comprising filtering the cells, cell debris, and growth media through a filter having pores ranging in size from about 0.45 µM to about 1.0 µM. Finally, for this aspect, it is preferred to include a virus inactivation step prior to combining the recovered recombinant HEF IDV protein in a composition. When an inactivation step is included, it is also preferred to include a neutralization step, as described above.

Additionally, the composition can include one or more pharmaceutical-acceptable or veterinary-acceptable carriers. As used herein, "a pharmaceutical-acceptable carrier" or "veterinary-acceptable carrier" includes any and all solvents, dispersion media, coatings, stabilizing agents, diluents, preservatives, antibacterial and antifungal agents, isotonic agents, adsorption delaying agents, and the like. In one preferred form, the composition provided herewith, contains HEF IDV protein recovered from in vitro cultured cells, wherein said cells were infected with a recombinant viral vector containing HEF IDV DNA and expressing HEF IDV protein, and wherein the cell culture was treated to inactivate the viral vector, and an equivalent concentration of a neutralization agent was added, and wherein both an adjuvant and physiological saline are also added. When included, the amount of physiological saline is preferably about 50 to about 90% (v/v), more preferably about 60 to 80% (v/v), still more preferably about 70% (v/v). Optionally, this method can also include the addition of a protectant. A protectant as used herein, refers to an anti-microbiological active agent, such as for example Gentamycin, Merthiolate, and the like. In particular adding a protectant is most preferred for the preparation of a multi-dose composition. Those anti-microbiological active agents are added in concentrations effective to prevent the composition of interest from any microbiological contamination or for inhibition of any microbiological growth within the composition of interest.

The methods and compositions of the present disclosure can also comprise the addition of any stabilizing agent, such as for example saccharides, trehalose, mannitol, saccharose and the like, to increase and/or maintain product shelf-life and/or to enhance stability.

In another aspect of the present disclosure, products resulting from the methods as described above are provided. In particular, the present disclosure relates to a composition of matter comprising recombinantly expressed HEF IDV protein. In some preferred forms, this composition of matter also comprises an agent suitable for the inactivation of viral vectors. Such products are useful as immunogenic compositions that induce an immune response and, more preferably, confers protective immunity against the clinical signs of HEF IDV infection. The composition generally comprises the polypeptide, or a fragment thereof, expressed by HEF as the antigenic component of the composition. Of course, it is understood that the HEF IDV polypeptide used in an immunogenic composition in accordance with the present disclosure can be derived in any fashion including isolation and purification, standard protein synthesis, and recombinant methodology.

Clinical signs of IDV infection are generally mild respiratory symptoms, but also include contribution to bovine respiratory disease and bovine respiratory disease complex. Additionally, viral load, antibody titers, apoptosis of cells, programmed cell death, and RNA load in tissues and cells (including epithelial and non-epithelial cells) from the as trachea, lung, nasal septum, nasal turbinates, bronchioles, and alveoli are also clinical signs of infection.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homologous sequence comprises at least a stretch of 50, even more preferably 100, even more preferably 250, even more preferably 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

According to a further aspect, HEF IDV protein is provided in the immunological composition at an antigen inclusion level effective for inducing the desired immune response, namely reducing the incidence of or lessening the severity of clinical signs resulting from IDV infection. Preferably, the HEF IDV protein inclusion level is at least 0.2 µg antigen/ml of the final immunogenic composition (µg/ml), more preferably from about 0.2 to about 400 µg/ml.

The polypeptide is incorporated into a composition that can be administered to an animal susceptible to IDV infection. In preferred forms, the composition may also include additional components known to those of skill in the art (see also Remington's Pharmaceutical Sciences. (1990). 18th ed. Mack Publ., Easton).

Those of skill in the art will understand that the composition herein may incorporate known injectable, physiologically acceptable, sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present disclosure can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants, are those described above.

According to a further aspect, the immunogenic composition of the present disclosure further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic compositions described herein can further include one or more other immunomodulatory agents such as, e. g., interleukins, interferons, or other cytokines. The immunogenic compositions can also include Gentamicin and Merthiolate. In another preferred embodiment, the present disclosure contemplates vaccine compositions comprising from about 1 ug/ml to about 60 µg/ml of antibiotics, and more preferably less than about 30 µg/ml of antibiotics.

It will be found that the immunogenic compositions comprising recombinant HEF IDV protein as provided herewith are very effective in reducing the severity of or incidence of clinical signs associated with IDV infections up to and including the prevention of such signs.

Another aspect of the present disclosure relates to a kit. Generally the kit includes a container comprising at least one dose of the immunogenic composition of HEF IDV nucleotide sequence or protein as provided herewith, wherein one dose comprises at least 100 µg/kg of the animal weight of the plasmid containing the HEF IDV nucleotide sequence or 2 µg HEF IDV protein. Said container can comprise from 1 to 250 doses of the immunogenic composition. In some preferred forms, the container contains 1, 10, 25, 50, 100, 150, 200, or 250 doses of the immunogenic composition of HEF IDV plasmid or protein. Preferably, each of the containers comprising more than one dose of the immunogenic composition of HEF IDV plasmid or protein further comprises an anti-microbiological active agent. Those agents are for example, antibiotics including Gentamicin and Merthiolate and the like. Thus, one aspect of the present disclosure relates to a container that comprises from 1 to 250 doses of the immunogenic composition of HEF IDV plasmid or protein, wherein one dose comprises at least 100 µg/kg of the animal weight of the plasmid containing the HEF IDV nucleotide sequence or 2 µg HEF IDV protein, and Gentamicin and/or Merthiolate, preferably from about 1 µg/ml to about 60 µg/ml of antibiotics, and more preferably less than about 30 µg/ml. In preferred forms, the kit also includes an instruction manual, including the information for the administration of at least one dose of the immunogenic composition of HEF IDV plasmid protein into animals, preferably cattle or pigs to lessen the incidence and/or severity of clinical symptoms associated with HEF IDV infection. Moreover, according to a further aspect, said instruction manual comprises the information of a second or further administration(s) of at least one dose of the immunogenic composition of HEF IDV plasmid or protein, wherein the second administration or any further administration is at least 14 days beyond the initial or any former administration. In some preferred forms, said instruction manual also includes the information, to administer an immune stimulant. Preferably, said immune stimulant shall be given at least twice. Preferably, at least 3, more preferably at least 5, and even more preferably at least 7 days are between the first and the second or any further administration of the immune stimulant. Preferably, the immune stimulant is given at least 10 days, preferably 15, even more preferably 20, and still even more preferably at least 22 days beyond the initial administration of the immunogenic composition of HEF IDV plasmid or protein. It is understood that any immune stimulant known to a person skilled in the art can also be used. "Immune stimulant" as used herein, means any agent or composition that can trigger a general immune response, preferably without initiating or increasing a specific immune response, for example the immune response against a specific pathogen. It is further instructed to administer the immune stimulant in a suitable dose. The kit may also comprise a second container, including at least one dose of the immune stimulant.

A further aspect of the present disclosure relates to the kit as described above, comprising the immunogenic composition of HEF IDV as provided herewith and the instruction manual, wherein the instruction manual further includes the information to administer the HEF IDV immunogenic composition together, or around the same time as, with an immunogenic composition that comprises an additional antigen effective for reducing the severity of or incidence of clinical signs related to another cattle or porcine pathogen. Preferably, the manual contains the information of when the HEF IDV containing composition and the immunogenic composition that comprises an additional antigen are administered.

A further aspect, relates to the use of any of the compositions provided herewith as a medicament, preferably as a veterinary medicament, even more preferably as a vaccine. Moreover, the present disclosure also relates to the use of any of the compositions described herein, for the preparation of a medicament for lessening the severity or incidence of clinical symptoms associated with IDV infection. Preferably, the medicament is for the prevention of IDV infection in cattle or swine.

A further aspect relates to a method for (1) the prevention of an infection, or re-infection with IDV or (2) the reduction in incidence or severity of or elimination of clinical signs or symptoms caused by IDV in a subject, comprising administering any of the immunogenic compositions provided herewith to a subject in need thereof. Preferably, the subject is a cow or pig. It is understood that the reduction is in comparison to a subject that has not received an administration of a composition of the present disclosure. Preferably, one dose or two doses of the immunogenic composition is/are administered, wherein one dose preferably comprises at least about 100 µg/kg of the animal weight of the plasmid containing the HEF IDV nucleotide sequence or 2 µg HEF IDV protein. A further aspect relates to the method of treatment as described above, wherein a second application of the immunogenic composition is administered. Preferably, the second administration is done with the same immunogenic composition, preferably having the same amount of HEF IDV protein. Preferably, the second administration is done at least 14 days beyond the initial administration, even more preferably at least 4 weeks beyond the initial administration. In preferred forms, the method is effective after just a single dose of the immunogenic composition and does not require a second or subsequent administration in order to confer the protective benefits upon the subject.

According to a further aspect, the present disclosure provides a multivalent combination vaccine which includes an immunological agent effective for reducing the incidence of or lessening the severity of IDV infection, and at least one immunological active component against another disease-causing organism in swine or cattle.

In particular the immunological agent effective for reducing the incidence of or lessening the severity of IDV infection is an IDV antigen. Preferably, said IDV antigen is a HEF IDV plasmid or protein as provided herewith, or any immunogenic composition as described above, that comprises HEF IDV plasmid or protein.

The terms "immunogenic protein", "immunogenic polypeptide" or "immunogenic amino acid sequence" as used herein refer to any amino acid sequence which elicits an immune response in a host against a pathogen comprising said immunogenic protein, immunogenic polypeptide or immunogenic amino acid sequence. An "immunogenic protein", "immunogenic polypeptide" or "immunogenic amino acid sequence" as used herein, includes the full-length sequence of any proteins, analogs thereof, or immunogenic fragments thereof. By "immunogenic fragment" is meant a fragment of a protein which includes one or more epitopes and thus elicits the immunological response against the relevant pathogen. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, New Jersey. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

Preferably the other disease-causing organism in swine is selected from the group consisting of: *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus; *Clostridium* spp., preferably *Cl. difficile, Cl. perfringens* types A, B, and C, *Cl. novyi, Cisepticum, Cl. tetani*; Coronavirus, preferably Porcine Respiratory Corona virus; *Eperythrozoonosis suis; Erysipelothrix rhsiopathiae; Escherichia coli; Haemophilus parasuis*, preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae*; and *Leptospira interrogans; Leptospira pomona; Leptospira tarassovi; Mycobacterium* spp. preferably *M. avium; M. intracellulare*; and *M. bovis; Mycoplasma hyopneumoniae* (*M. hyo*); *Pasteurella multocida*; Porcine cytomegalovirus; Porcine Parvovirus; Porcine Reproductive and Respiratory Syndrome (PRRS) Virus; Pseudorabies virus; Rotavirus; *Salmonella* spp.; preferably *S. thyhimurium*; and *S. choleraesuis; Staph. hyicus; Staphylococcus* spp. preferably *Streptococcus* spp., preferably *Strep. suis*; Swine herpes virus; Swine Influenza Virus; Swine pox virus; Swine pox virus; Vesicular stomatitis virus; Virus of vesicular exanthema of swine; *Leptospira Hardjo*; and/or *Mycoplasma hyosynoviae.*

An "immunological active component" as used herein means a component that induces or stimulates the immune response in an animal to which said component is administered. According to a preferred embodiment, said immune response is directed to said component or to a microorganism comprising said component. According to a further preferred embodiment, the immunological active component is an attenuated microorganism, including modified live virus (MLV), a killed-microorganism or at least an immunological active part of a microorganism.

"Immunological active part of a microorganism" as used herein means a protein-, sugar-, and or glycoprotein containing fraction of a microorganism that comprises at least one antigen that induces or stimulates the immune response in an animal to which said component is administered. According to a preferred embodiment, said immune response is directed to said immunological active part of a microorganism or to a microorganism comprising said immunological active part.

The present disclosure also relates to vaccines comprising a nucleotide sequence of HEF IDV, or a homologue or fragment thereof, and an acceptable pharmaceutical or veterinary vehicle. In one embodiment of the disclosure, the nucleotide sequence is selected from, SEQ ID NO. 2 or a homologue or fragment thereof. In another embodiment of the disclosure, the homologue has at least 85, 90, 91, 92, 93, 94, 95, 96, 97, 98, 99, 99.5, or 100% sequence identity to SEQ ID NO. 2. In yet another embodiment, the vaccine further comprises an adjuvant.

A further aspect of the present disclosure relates to vaccines comprising a vector and an acceptable pharmaceutical or veterinary vehicle, the vector comprising a nucleotide sequence of HEF IDV, preferably SEQ ID NO. 2, or a homologue or fragment thereof.

Additionally, the present disclosure relates to methods of immunizing a mammal against IDV comprising administering to a mammal an effective amount of a vaccine or immunogenic composition described above.

The present disclosure likewise relates to nucleotide sequences, characterized in that they are selected from: a) a nucleotide sequence of SEQ ID NO. 2; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide or nucleic acid sequence will be understood according to the present disclosure as meaning both a double-stranded or single-stranded DNA in the monomeric and dimeric (so-called in tandem) forms and the transcription products of said DNAs.

Complementary nucleotide sequence of a sequence of the disclosure is understood as meaning any DNA whose nucleotides are complementary to those of the sequence of the disclosure, and whose orientation is reversed (antiparallel sequence).

Hybridization under conditions of stringency with a nucleotide sequence according to the disclosure is understood as meaning a hybridization under conditions of temperature and ionic strength chosen in such a way that they allow the maintenance of the hybridization between two fragments of complementary DNA.

Among the nucleotide sequences according to the disclosure, those are likewise preferred which can be used as a primer or probe in methods allowing the homologous sequences according to the disclosure to be obtained, these methods, such as the polymerase chain reaction (PCR), nucleic acid cloning and sequencing, being well known to the person skilled in the art.

Among said nucleotide sequences according to the disclosure, those are again preferred which can be used as a primer or probe in methods allowing the presence of IDV or one of its variants such as defined below to be diagnosed.

Modified nucleotide sequence will be understood as meaning any nucleotide sequence obtained by mutagenesis according to techniques well known to the person skilled in the art, and containing modifications with respect to the normal sequences according to the disclosure, for example mutations in the regulatory and/or promoter sequences of polypeptide expression, especially leading to a modification of the rate of expression of said polypeptide or to a modulation of the replicative cycle.

Modified nucleotide sequence will likewise be understood as meaning any nucleotide sequence coding for a modified polypeptide such as defined below.

In the present description, the terms polypeptide, peptide and protein are interchangeable.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. These equivalent amino acids can be determined either by depending on their structural homology with the amino acids which they substitute, or on results of comparative tests of biological activity between the different polypeptides, which are capable of being carried out. By way of example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

The disclosure likewise relates to nucleotide sequences utilizable as a primer or probe, characterized in that said sequences are selected from the nucleotide sequences according to the disclosure.

The disclosure additionally relates to the use of a nucleotide sequence according to the disclosure as a primer or probe for the detection and/or the amplification of nucleic acid sequences.

The nucleotide sequences according to the disclosure can thus be used to amplify nucleotide sequences, especially by the PCR technique (polymerase chain reaction) (Erlich, 1989; Innis et al., 1990; Rolfs et al., 1991; and White et al., 1997). These oligodeoxyribonucleotide or oligoribonucleotide primers advantageously have a length of at least 8 nucleotides, preferably of at least 12 nucleotides, and even more preferentially at least 20 nucleotides. Other amplification techniques of the target nucleic acid can be advantageously employed as alternatives to PCR.

The nucleotide sequences of the disclosure, in particular the primers according to the disclosure, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

The polynucleotides of the disclosure can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al. as well as by Stone et al. in 1996.

The disclosure likewise relates to a pharmaceutical composition comprising a compound selected from the following compounds: a) a nucleotide sequence according to the disclosure; b) a polypeptide according to the disclosure; or c) a vector transformed according to the disclosure; possibly in combination with a pharmaceutically acceptable carrier and, if need be, with one or more adjuvants of the appropriate immunity.

The disclosure also relates to an immunogenic and/or vaccine composition, characterized in that it comprises a compound selected from the following compounds: a) a nucleotide sequence according to the disclosure; b) a polypeptide according to the disclosure; or c) a vector according to the disclosure.

The disclosure is likewise directed at a pharmaceutical composition according to the disclosure, for the prevention or the treatment of an infection by IDV.

It is understood that "prevention" as used in the present disclosure, includes the complete prevention of infection by a HEF IDV, but also encompasses a reduction in the severity of or incidence of clinical signs associated with or caused by IDV infection. Such prevention is also referred to herein as a protective effect.

The disclosure likewise concerns the use of a composition according to the disclosure, for the preparation of a medicament intended for the prevention or the treatment of infection by IDV.

The compositions according to the disclosure will contain an effective quantity of the compounds of the disclosure, that is to say in sufficient quantity of said compound(s) allowing the desired effect to be obtained. The person skilled in the art will know how to determine this quantity, as a function, for example, of the age and of the weight of the individual to be treated, of the state of advancement of the pathology, of the possible secondary effects and by means of a test of evaluation of the effects obtained on a population range, these tests being known in these fields of application.

According to the disclosure, said vaccine combinations will preferably be combined with a pharmaceutically or veterinary acceptable carrier and, if need be, with one or more adjuvants of the appropriate immunity.

Vaccines and immunogenic compositions according to the disclosure can likewise be prepared in the form of a composition containing a vector according to the disclosure, placed under the control of regulation elements allowing its expression in man or animal. Such a vaccine will advantageously comprise, apart from the recombinant vector, a saline solution, for example a sodium chloride solution.

These compounds can be administered by the systemic route, in particular by the intravenous route, by the intramuscular, intradermal or subcutaneous route, or by the oral or nasal route. In some embodiments, the vaccine composition comprising plasmids or polypeptides according to the disclosure will be administered by injection or intranasally, through the food, or by nebulization once or several times, staggered over time.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present disclosure is administered in an amount that is protective or provides a protective effect against IDV infection.

Another preferred vaccine of the present disclosure utilizes suitable plasmids for delivering the HEF IDV nucleotide sequence to an animal in need thereof including to cattle or pigs. In contrast to the traditional vaccine that uses live or killed cell culture propagated whole virus, this disclosure provides for the direct inoculation of cattle or pigs with the plasmid DNA containing the HEF IDV nucleotide sequence.

The vaccine can be administered in a single dose or in repeated doses with single doses being preferred. Single dose vaccines provide protection after a single dose without the need for any booster or subsequent dosages. Protection can include the complete prevention of clinical signs of infection, or a lessening of the severity, duration, or likelihood of the manifestation of one or more clinical signs of infection. Dosages may range, for example, from about 1 microgram to about 1,000 micrograms/kg of the animal of the plasmid DNA containing the HEF IDV sequence, preferably 100 to 200 micrograms/kg of the animal of the HEF IDV DNA. Methods are known in the art for determining or titrating suitable dosages of active antigenic agent to find minimal effective dosages based on the weight of the animal, concentration of the antigen and other typical factors. Preferably, the HEF IDV DNA is used as a vaccine.

Desirably, the vaccine is administered to an animal not yet exposed to IDV.

When administered as a liquid, the present vaccine may be prepared in the form of an aqueous solution, syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives that can be employed in the present vaccine include, but are not limited to, dextrose, conventional antioxidants and conventional chelating agents such as ethylenediamine tetraacetic acid (EDTA). Parenteral dosage forms must also be sterilized prior to use.

It should be appreciated that all scientific and technological terms used herein have the same meaning as commonly understood by those of ordinary skill in the art.

Another aspect of the present disclosure is the preparation of the combination vaccine(s) or immunogenic compositions. Such combinations can be between the different vaccine components described herein. For example, a vaccine of the present disclosure can include both protein portions and DNA portions of HEF IDV, as described herein, which are administered concurrently or separately. Additionally, the combinations can be between the HEF IDV vaccine components described herein and antigens of other disease-causing organisms, such as those described above.

According to a further aspect, the vaccine or immunogenic composition is first dehydrated. If the composition is first lyophilized or dehydrated by other methods, then, prior to vaccination, said composition is rehydrated in aqueous (e.g. saline, PBS (phosphate buffered saline)) or non-aqueous solutions (e.g. oil emulsion (mineral oil, or vegetable/metabolizable oil based/single or double emulsion based), aluminum-based, carbomer based adjuvant).

According to the present disclosure, an effective amount of a combination vaccine administered to an animal in need thereof provides effective immunity or a protective effect against microbiological infections caused by IDV and at least one further pathogen. Preferred combinations of antigens for the treatment and prophylaxis of microbiological diseases in cattle and pigs are listed above.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 4A is a photograph illustrating IDV RNA+ cells (black silver grains in radioautographs) in lung tissues detected using in situ hybridization from the area in the left red box in FIG. 4B;

FIG. 4B is a photograph illustrating IDV RNA+ cells (black silver grains in radioautographs) in lung tissues detected using in situ hybridization;

FIG. 4C is a photograph illustrating IDV RNA+ cells (black silver grains in radioautographs) in lung tissues detected using in situ hybridization from the area in the right red box in FIG. 4B;

FIG. 4D is a photograph illustrating IDV RNA+ cells (black silver grains in radioautographs) in lung tissues detected using in situ hybridization from the area in the left red box in FIG. 4E;

FIG. 4E is a photograph illustrating IDV RNA+ cells in lung tissues detected using in situ hybridization (black silver grains in radioautographs);

FIG. 4F is a photograph illustrating IDV RNA+ cells (black silver grains in radioautographs) in lung tissues detected using in situ hybridization from the area in the right red box in FIG. 4E;

FIG. 4G is a photograph illustrating IDV RNA+ cells (black silver grains in radioautographs) in lung tissues detected using in situ hybridization from the area in the left red box in FIG. 4H;

FIG. 4H is a photograph illustrating IDV RNA+ cells in lung tissues detected using in situ hybridization (black silver grains in radioautographs);

FIG. 4I is a photograph illustrating IDV RNA+ cells (black silver grains in radioautographs) in lung tissues detected using in situ hybridization from the area in the right red box in FIG. 4H;

FIG. 4J is a photograph illustrating IDV RNA+ cells (black silver grains in radioautographs) in lung tissues detected using in situ hybridization from the area in the left red box in FIG. 4K;

FIG. 4K is a photograph illustrating IDV RNA+ cells in lung tissues detected using in situ hybridization (black silver grains in radioautographs);

FIG. 4L is a photograph illustrating IDV RNA+ cells (black silver grains in radioautographs) in lung tissues detected using in situ hybridization from the area in the right red box in FIG. 4K;

FIG. 6A is a photograph of immunohistochemically stained lung epithelial tissue;

FIG. 6B is a photograph of immunohistochemically stained lung epithelial tissue;

FIG. 6C is a photograph of immunohistochemically stained lung epithelial tissue;

FIG. 6D is a photograph of immunohistochemically stained lung epithelial tissue;

FIG. 6E is a photograph of immunohistochemically stained lung epithelial tissue;

FIG. 6F is a photograph of immunohistochemically stained lung epithelial tissue;

FIG. 7A is a micrograph of lung epithelial cells that received the IDV D/660 vaccine and were challenged intranasally with IDV D/660;

FIG. 7B is a micrograph of lung epithelial cells that received the IDV D/660 vaccine and were challenged intranasally with IDV D/660;

FIG. 7C is a micrograph of lung epithelial cells that received a sham vaccine and were challenged intranasally with IDV D/660;

FIG. 7D is a micrograph of lung epithelial cells that received a sham vaccine and were challenged intranasally with IDV D/660;

FIG. 7E is a micrograph of lung epithelial cells that received a sham vaccine and were challenged intranasally with IDV D/660;

FIG. 7F is a micrograph of lung epithelial cells that received a sham vaccine and were challenged intranasally with IDV D/660;

FIG. 7G is a micrograph of lung epithelial cells that received the IDV D/OK vaccine and were challenged intranasally with IDV D/OK;

FIG. 7H is a micrograph of lung epithelial cells that received the IDV D/OK vaccine and were challenged intranasally with IDV D/OK;

FIG. 7I is a micrograph of lung epithelial cells that received a sham vaccine and were challenged intranasally with IDV D/OK;

FIG. 7J is a micrograph of lung epithelial cells that received a sham vaccine and were challenged intranasally with IDV D/OK;

FIG. 7K is a micrograph of lung epithelial cells that received a sham vaccine and were challenged intranasally with IDV D/OK;

FIG. 7L is a micrograph of lung epithelial cells that received a sham vaccine and were challenged intranasally with IDV D/OK;

DETAILED DESCRIPTION

Figure 1:
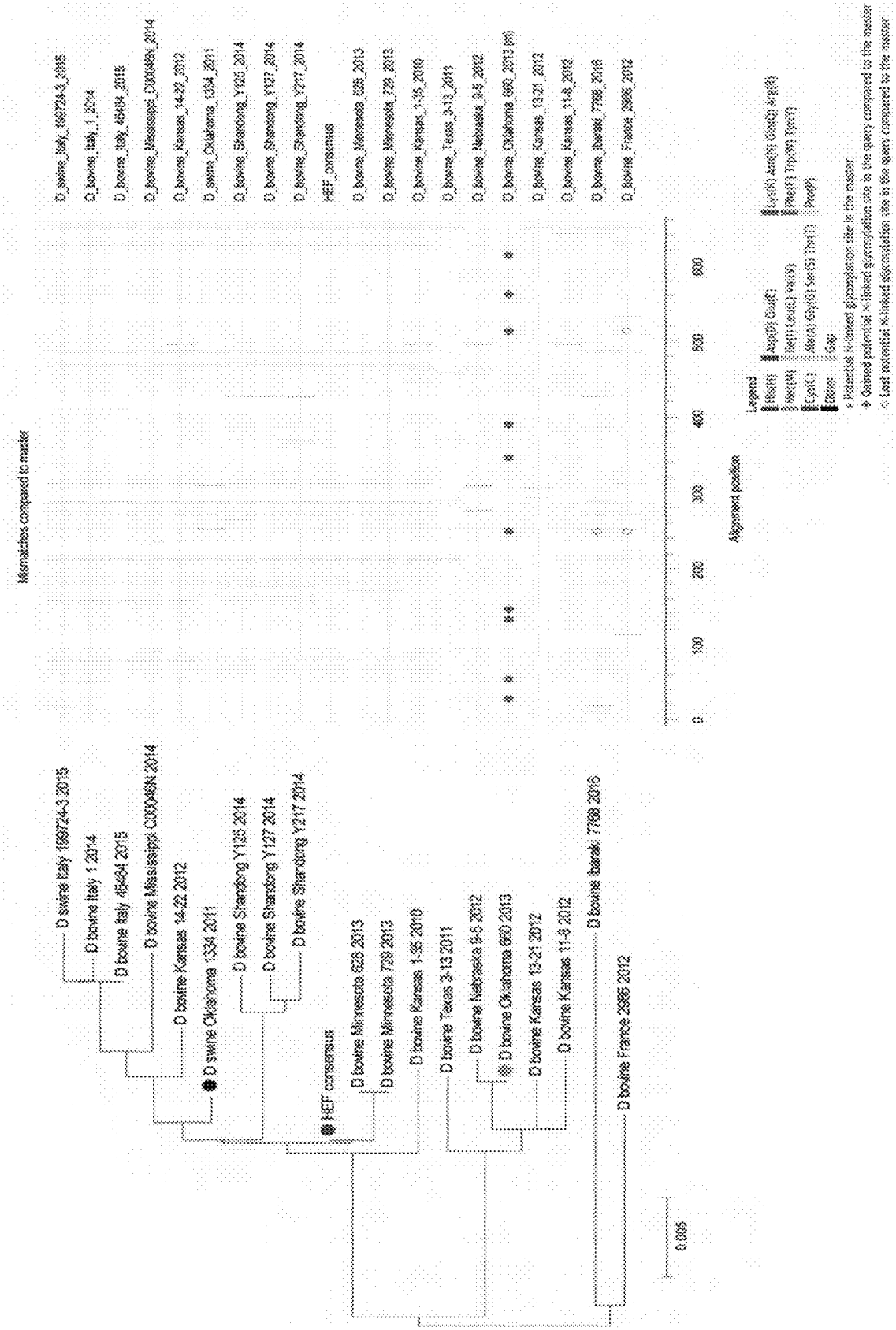
FIG. 1 is a depiction of the phylogenetic analysis of ConD-HEF protein.

The following detailed description and examples set forth preferred materials and procedures used in accordance with the present disclosure. It is to be understood, however, that this description and these examples are provided by way of illustration only, and nothing therein shall be deemed to be a limitation upon the overall scope of the present disclosure. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure unless noted otherwise. All parts and percents referred to herein are on a weight basis and all temperatures are expressed in degrees centigrade unless otherwise specified. Further unless noted otherwise, all components of the disclosure are understood to be disclosed to cover "comprising", "consisting essentially of", and "consisting of" claim language as those terms are commonly used in patent claims.

Example 1

Materials and Methods

Animals and Animal Procedures

Guinea pig experiments were conducted by following the protocol approved by the Institutional Animal Care and Use Committees (IACUC) at UNL. Twenty-four specific-pathogen-free (SPF) or viral-antibody-free (VAF), and approximately 3-month-old female guinea pigs of the Dunkin-Hartley strain (Elm Hill Labs, MA, USA) were used in this study. The animals were individually housed and were ear tagged after a 1-week acclimation period.

Consensus DNA Vaccine Design and Preparation

To develop a vaccine that could prevent both lineages of IDV infection, a consensus HEF DNA vaccine was designed. The HEF amino acid sequences of 19 IDVs isolated between 2011 and 2016 were downloaded from GenBank, from which the consensus sequence (664 amino acids) (SEQ ID NO. 1) was calculated using BioEdit (Version 7.2.0). Codons of the consensus HEF gene were optimized for efficient expression in mammalian cells by using an online tool (JCat found online at jcat.de). After codon optimization, the consensus HEF gene (SEQ ID NO. 2) was synthesized (GENEWIZ LLC, NJ, USA) and inserted into the pJW4303 expression vector, which was kindly provided by Dr. Shan Lu (University of Massachusetts Medical School, Massachusetts, USA). The constructed plasmid with the HEF insert was designated as FluD-Vax and the same plasmid without the HEF insert was used as vector control. FluD-Vax and control plasmid DNA were prepared by using an EndoFree Plasmid Giga Kit (Cat #12391, Qiagen, Germany) for guinea pig vaccination.

Experiment Design

Guinea pigs were randomly divided into four groups (6 per group). Animals in vaccine groups (Vac 1 and Vac 2) were inoculated into tibialis anterior muscle with FluD-Vax (200 μg/animal) 4 times at 4-week intervals, and animals in the control groups (Ctr 1 and Ctr 2) were inoculated with the same quantity of control plasmid DNA in parallel. A detailed vaccination schedule is shown in Table 1.

IDV Challenge and Sample Collection

To test the protective efficacy of FluD-Vax against two lineages of IDV, animals in the Vac 1 and Ctr 1 groups were challenged with a IDV D/OK lineage-representative strain (D/swine/Oklahoma/1334/2011, D/OK) and Vac 2 and Ctr 2 groups were challenged with a D/660 lineage-representative strain (D/bovine/Oklahoma/660/2013, D/660) (Table 1). IDV stocks were prepared as previously reported (11) and diluted in PBS containing 100 units/ml penicillin, 100 μg/ml streptomycin, and 0.3% BSA (PBS-PS-BA). A 300 μl volume of IDV inoculum containing 3E5 $TCID_{50}$ was instilled into the nostrils (150 μl on each side) at 30 days post final immunization. After IDV challenge, the animal head and nose were kept slightly elevated with respect to the rump for 15 minutes to prevent the inoculum from flowing out of the nostrils.

Body weight and temperature of the guinea pigs were monitored daily for up to 7 days starting from the day of IDV challenge but before virus inoculation (day 0). At 5 and 7 days post challenge, 2 and 4 animals from each group were euthanized, respectively. Immediately after euthanasia, blood, nasal turbinate, septum, soft palate, trachea, lung, and draining lymph node were collected. Half of collected tissues were fixed in 4% paraformaldehyde (PFA) and the remaining half were snap frozen immediately in liquid nitrogen.

IDV Hemagglutination Inhibition (HI) Assay

Guinea pig sera were treated with receptor-destroying enzyme (RDE; Denka Seiken, Tokyo, Japan) before the HI assay was performed. The RDE treatment was done according to the manufacturer's protocol and the hemagglutination inhibition assay was performed using our previously described method (11). The HI assay was performed against the two representative IDV lineage viruses (D/swine/Oklahoma/1334/2011; D/bovine/Oklahoma/660/2013) using 1% turkey red blood cells (RBCs) (Lampire Biological Laboratories, Pipersville, Pa., USA).

Real-Time qRT-PCR

Primers and probe were designed to target a conserved region of the NP gene (Table 2). A recombinant plasmid, containing the full-length NP sequence of the IDV strain D/swine/Oklahoma/1334/2011 (accession number: JQ922306), was serially diluted and used as qRT-PCR standard. Snap-frozen lung tissue was put into 2 ml tube pre-filled with stainless steel beads (RNA-WIST01, WISBIOMED LLC, CA) and homogenized for 2 min using a MiniBeadBeater-16 (BioSpec Products, Inc. OK). RNA from homogenized lung tissues and plasma specimens was extracted using a QIAamp Viral RNA Mini Kit (Cat #52906, Qiagen, Germany). The qRT-PCR reaction was performed in 20 μl containing 1× TaqMan® Fast Virus 1-Step Master Mix (Cat #4444434, Thermo Fisher Scientific, USA), 500 nM of each primer, 250 nM of probe, and 5 μl total RNA extracted from supernatants of homogenized guinea pig lung tissues. at 50° C. for 5 min, followed by RT inactivation/initial denaturation step at 95° C. for 20 s and 45 cycles of denaturation at 95° C. for 3 s and annealing/extension at 60° C. for 30 s. Fluorescence signal was detected after the annealing/extension step at each cycle. All PCR assays were performed on the CFX96 Real-Time PCR System (Bio-Rad, California, USA). The lower limit of detection for this method was verified to be around 10 copies/reaction.

TABLE 1

Guinea pig vaccination schedule

| Group | week 1 | week 4 | week 8 | week 12 | week 16 |
| --- | --- | --- | --- | --- | --- |
| Vac 1(n = 6) | ConD HEF, 200 μg each | ConD HEF, 200 μg each | ConD HEF, 200 μg each | ConD HEF, 200 μg each | Challenged with IDV-D/OK, 3E5 $TCID_{50}$/300 μl |
| Ctr 1(n = 6) | mock, 200 μg each | mock, 200 μg each | mock, 200 μg each | mock, 200 μg each | |
| Vac 2(n = 6) | ConD HEF, 200 μg each | ConD HEF, 200 μg each | ConD HEF, 200 μg each | ConD HEF, 200 μg each | Challenged with IDV-D/660, 3E5 $TCID_{50}$/300 μl |
| Ctr 2(n = 6) | mock, 200 μg each | mock, 200 μg each | mock, 200 μg each | mock, 200 μg each | |

TABLE 2

Primers and probe for Real-Time PCR

| .ligo | Sequence | SEQ ID NO. | Position[a] |
|---|---|---|---|
| NP_Forward | 5'-AAGCGACGTTCCAAGAACTG | 3 | 1542-1561 |
| NP_Reverse | 5'-GGGACTGCAACAGAACCATC | 4 | 1716-1697 |
| NP_probe | 5'Fam-TGCTCCGGCACCTTGCCTTCC-3'Tamra | 5 | 1647-1627 |

[a]Numbering is from the sequence of D/swine/.klahoma/1334/2011 PB1 gene, accession number: JQ922306.

In Situ Hybridization (ISH)

IDV in respiratory tract tissues was detected using in situ hybridization (ISH) with radioactive isotopes of sulfur ($^{35}$S) labeled negative-sense RNA probes of HEF and nucleoprotein (NP). HEF (1071 bp) and NP (1024 bp) cDNA templates were amplified from D/OK HEF and NP gene plasmids using PCR with the following primer pairs containing polymerase sequences: HEF-forward primer-T7: AACGTGTAATACGACTCACTATAGGG AGGGGCTTCGTTGATGTTGT (SEQ ID No. 6) and HEF reverse primer-SP6: AACTGGATTTAGGTGACAC-TATAG AAGATCCTTGTTGCTGGCGT (SEQ ID NO. 7), NP-forward primer-T7: AACGTGTAATACGACTCAC-TATAGGG TGGCAAGCAAAAAGAACGGG (SEQ ID NO. 8), and NP-reverse primer-5P6: AACTGGATT-TAGGTGACACTATAGA CCTCTTTTCTTGGGCTGGGA (SEQ ID NO. 9). Negative sense riboprobes from HEF and NP were generated by in vitro run-off transcription with SP6 RNA polymerase and were used for detection of viral transcripts. Six-micron tissue sections were cut and ISH was conducted by following our previously published method (18). Slides were exposed for 3 days in radioautography and counter-stained with hematoxylin and eosin. Tissue sections were digitized using Scanscope and IDV RNA positivity was reviewed by two investigators independently. The specificity of IDV riboprobes were confirmed using HIV-1 riboprobes as a negative control probe and rhesus lung tissues as negative control tissues.

Combined Immunohistochemical Staining and ISH

To determine the cell type of IDV infected cells, a combination of immunohistochemical staining (IHCS) and ISH was performed as previously described (19). A pan-cytokeratin rabbit polyclonal antibody (MA5-13203, 1:150, Invitrogen) and diaminobenzidine (DAB) with the Dako Envision and Peroxidase kit was used for IHCS. Stained tissue sections were digitized using Scanscope and viral RNA ISH signal and immunohistochemically stained epithelial cell signal was viewed in single color channel and combined color channels using Aperio's Spectrum Plus analysis program (version 9.1; Aperio ePathology Solutions).

In Situ Cell Death Detection by TUNEL Assay

To detect apoptotic cell death in lung tissues, terminal deoxynucleotidyl transferase dUTP nick end labeling (TUNEL) assay was performed as we previously described (19). In situ cell death detection AP Kit (Cat #11-684 809 910, Roche) and AP substrate (RNAscope® 2.0 HD Detection Kit, RED, ACD) were used to immunochemically detect TUNEL-positive apoptotic cells as red color signals. The stained tissue sections were digitized using Scanscope.

Statistical Analysis

Statistical analyses were performed using GraphPad Prism 6.0 (GraphPad Software, California, USA). The HI antibody titers of two groups at multiple time points were compared by two-way ANOVA. Data are presented as mean±SD in FIG. 2 and FIG. 3. P<0.05 was considered as statistically significant.

Results

Phylogenetic and Antigenic Analysis of Consensus IDV HEF Protein

IDV is similar to ICV in that it uses only one hemagglutinin-esterase-fusion glycoprotein (HEF) spike for receptor binding, receptor destruction, and membrane fusion (14). The surface HEF thus represents a key protective immunogen for the development of a preventive vaccine. Two lineages of IDVs are primarily responsible for current IDV global infections (1, 3, 13). Furthermore, these two distinct lineages of IDVs can also co-infect the same animals (3, 20). To develop an IDV vaccine that could prevent infection from both lineages of IDV, we designed and constructed an IDV HEF consensus gene (ConD-HEF) based vaccine, named as FluD-Vax. Phylogenetic analysis showed that the amino acid sequence of ConD-HEF resembles both lineages, but is closer to the lineage represented by strain D/swine/Oklahoma/1334/2011 (D/OK) than the lineage represented by strain D/bovine/Oklahoma/660/2013 (D/660) (FIG. 1). As shown in FIG. 1, the phylogenetic relationship of HEF amino acid sequences between consensus vaccine (ConD-HEF) and 19 IDVs isolates was illustrated in a N-J phylogeny plot (left panel) and a Highlighter plot (right panel). In the phylogeny plot, the consensus HEF was depicted as a closed red circle, D/swine/Oklahoma/1334/2011 (D/OK) as an open blue circle and D/bovine/Oklahoma/660/2013 (D/660) as an open green circle. Bar length represented 0.005 amino acid substitutions per site. Amino acid polymorphisms in the highlighter plot were indicated by a colored mark. The phylogenetic distance (average substitutions per amino acid) of ConD-HEF to D/OK is 0.5% and D/660 is 2.6%. The antigenicity of the consensus HEF protein expressed by the FluD-Vax was assessed by Western-blotting. Our data showed that both the full-length HEF and the cleaved HEF1 (16) could be recognized by rabbit anti-IDV sera.

Figure 2A:
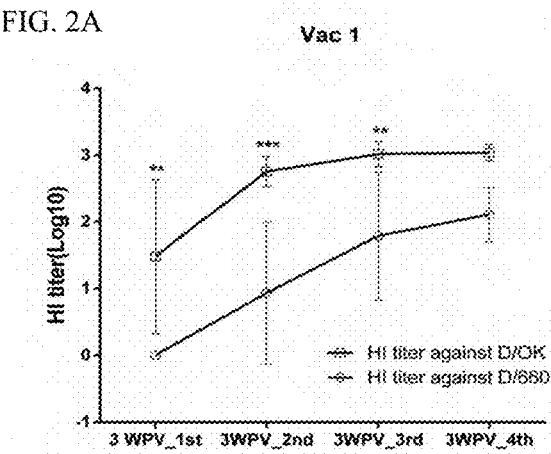
FIG. 2A is a graph illustrating HI antibody responses in peripheral blood induced by ConD-HEF vaccine and evaluated by hemagglutination inhibition (HI) assay.
Figure 2B:
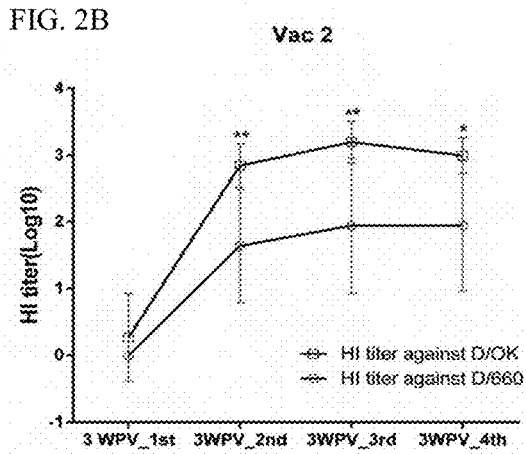
FIG. 2B is a graph illustrating HI antibody responses in peripheral blood induced by the second ConD-HEF vaccine group and evaluated by hemagglutination inhibition (HI) assay.
Figure 2C:
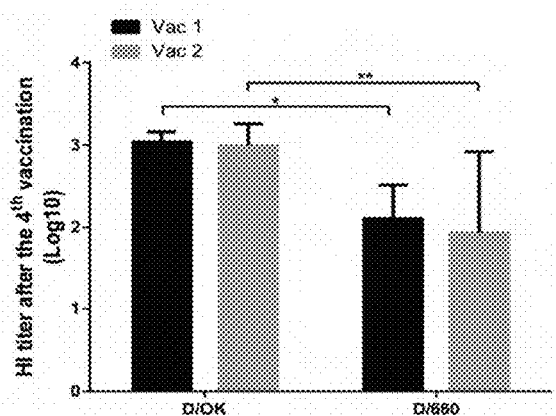
FIG. 2C is a graph illustrating the mean HI antibody titers of the two vaccine groups at 3 weeks post final vaccination.
Figure 2D:
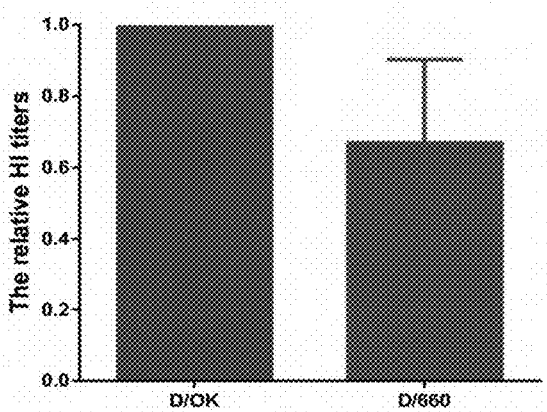
FIG. 2D is a graph illustrating the relative HI titers that were calculated by normalizing D/660 HI titer to D/OK HI titer for each individual animal.

FluD-Vax elicited robust HI antibody responses against both D/OK and D/660 lineages As illustrated in Table 1, the guinea pigs in the vaccine and control groups were immunized with FluD-Vax or control plasmid DNA, respectively, 4 times at 4-week intervals. Peripheral blood was collected at 3 weeks post each vaccination for evaluation of HEF-specific neutralizing antibodies against D/OK and D/660 using hemagglutination inhibition (HI) assay. The HI antibody titers against both IDVs increased significantly after the second immunizations and peaked after the third immunization. The mean titer of HI antibodies against D/OK was higher than D/660 after each vaccine immunization (FIGS. 2A and 2B). Control groups did not generate a detectable HI antibody response at any time point (Data not shown). ConD-HEF vaccine induced robust HI antibody responses against D/OK and D/660 in both vaccine groups. However, the mean magnitudes against D/OK were higher than against D/660 over the course of immunization (*: P<0.1, : P<0.01, *: P<0.001). Interestingly, after the final vaccination, the mean HI antibody titers to D/OK or D/660 between the two vaccine groups (Vac 1 and Vac 2) were similar (FIG. 2C), indicating that our vaccine induced a similar-level of immune responses between the Vac1 and Vac2 groups. In addition, we also calculated the relative HI antibody titers of D/660 to D/OK and found the mean ratio of D/660 versus D/OK HI titers was 0.67 (FIG. 2D). The relative HI titers were calculated by normalizing D/660 HI titer to D/OK HI titer for each individual animal. Error bars represent standard deviations.

Figure 2E:
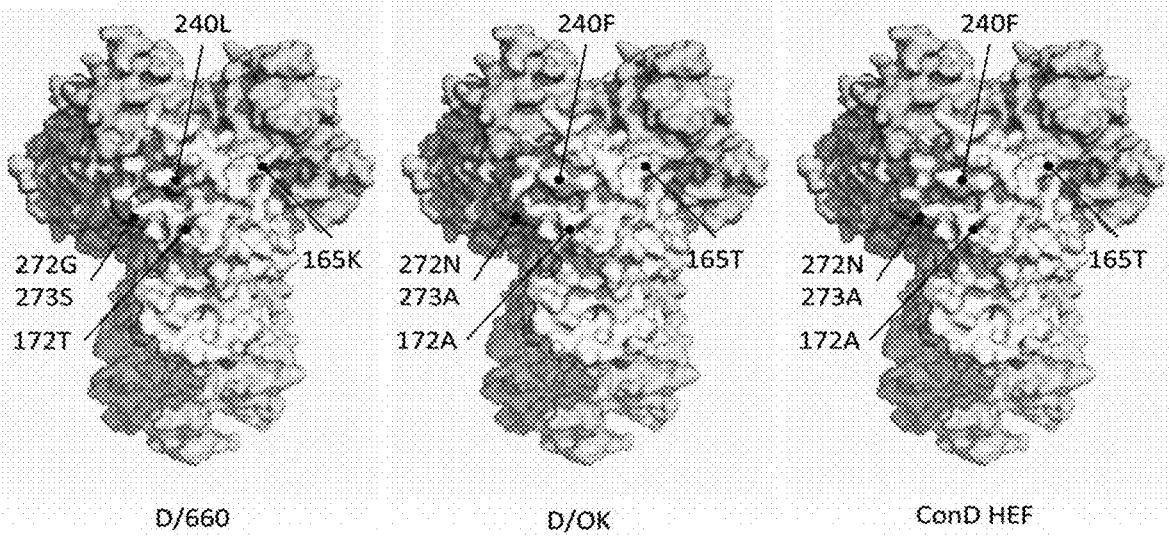
FIG. 2E provides depictions of the hemagglutinin-esterase-fusion protein (HEFP) structure of influenza D virus (PDB ID 5e64)

To generate the pictures in FIG. 2E, the hemagglutinin-esterase-fusion protein (HEFP) structure of influenza D virus (PDB ID 5e64) was selected as a template, and all models received QMEAN value −0.45. The trimer formation was made refereeing HEFP structure of influenza C virus (1flc). One subunit was colored in white, while other two were in light green. Graphics were prepared by the PyMOL Molecular Graphics System, Version 1.8 Schrodinger, LLC (New York, N.Y., USA).

Efficacy of FluD-Vax Protection Against IDV Infections

To evaluate the protective efficacy of consensus FluD-Vax vaccine against two lineages of IDV infection, the guinea pigs in the Vac 1 and Ctr 1 groups were challenged with IDV D/OK and the Vac 2 and Ctr 2 groups were challenged with IDV D/660. A minimal loss of body weight (<5% on average) post viral challenge occurred in all groups with a slightly more reduction in body weight observed in the vaccine group after D/OK challenge compared to the control group. The body temperature of animals in both vaccine and control groups remained stable without significant fluctuation FIG. 3).

Figure 3:
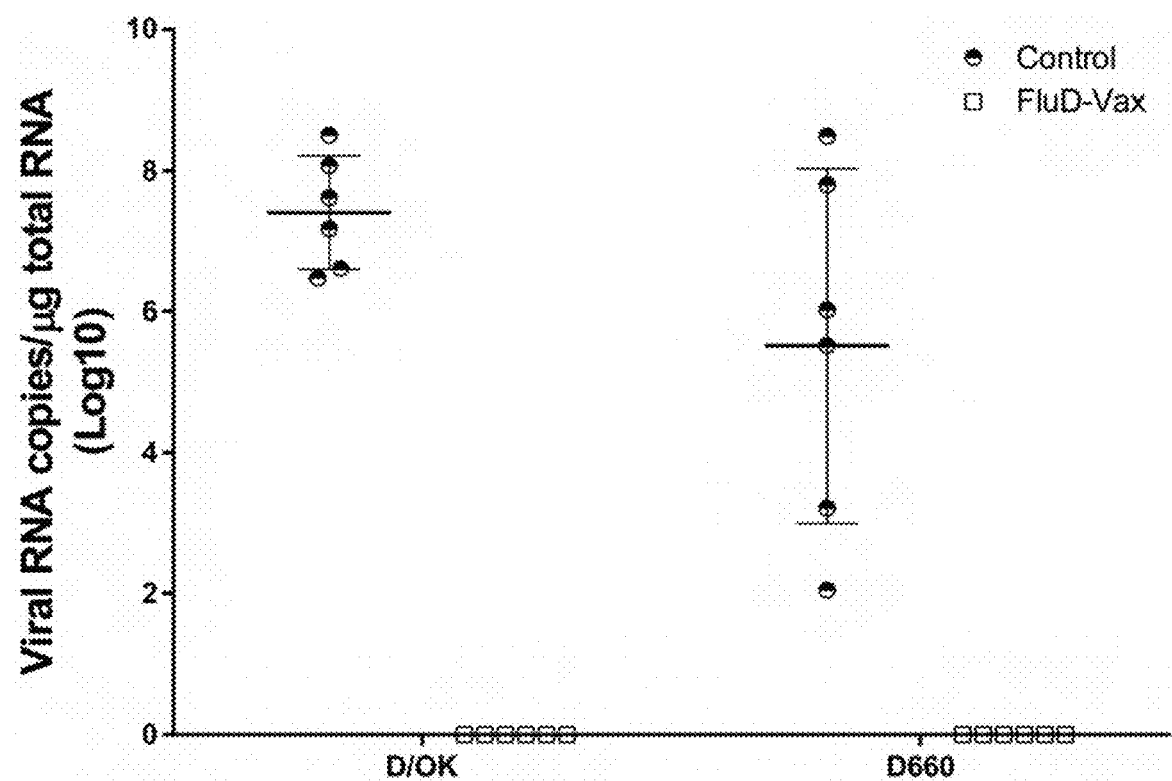
FIG. 3 is a graph illustrating IDV RNA load in lung tissues quantified using qRT-PCR.
Figures 5A, 5B, 5C, 5D:
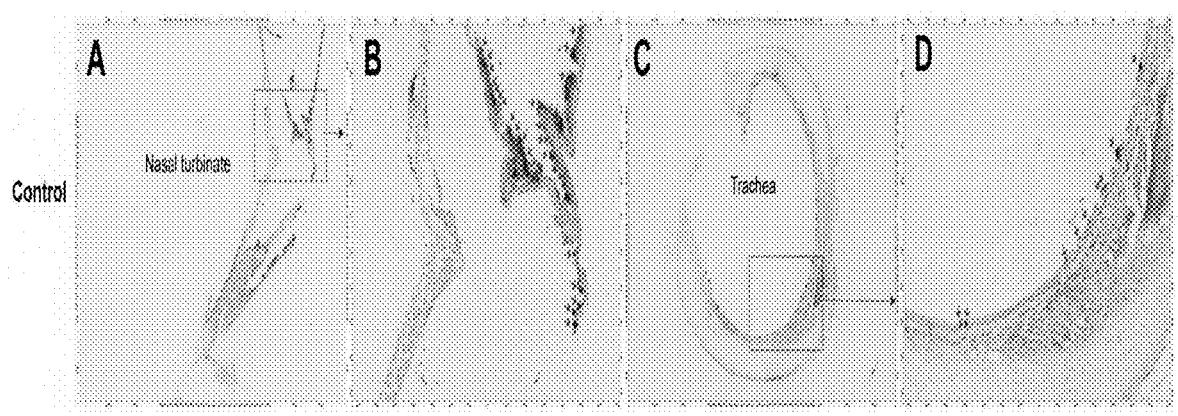
FIG. 5A is a photograph illustrating IDV RNA+ cells in nasal turbinate tissue in the control group detected using in situ hybridization.
FIG. 5B is a magnified photograph of the area in the red box in FIG. 5A.
FIG. 5C is a photograph illustrating IDV RNA+ cells in tracheal tissue in the control group detected using in situ hybridization.
FIG. 5D is a magnified photograph of the area in the red box in FIG. 5C.
Figures 5E, 5F, 5G, 5H:
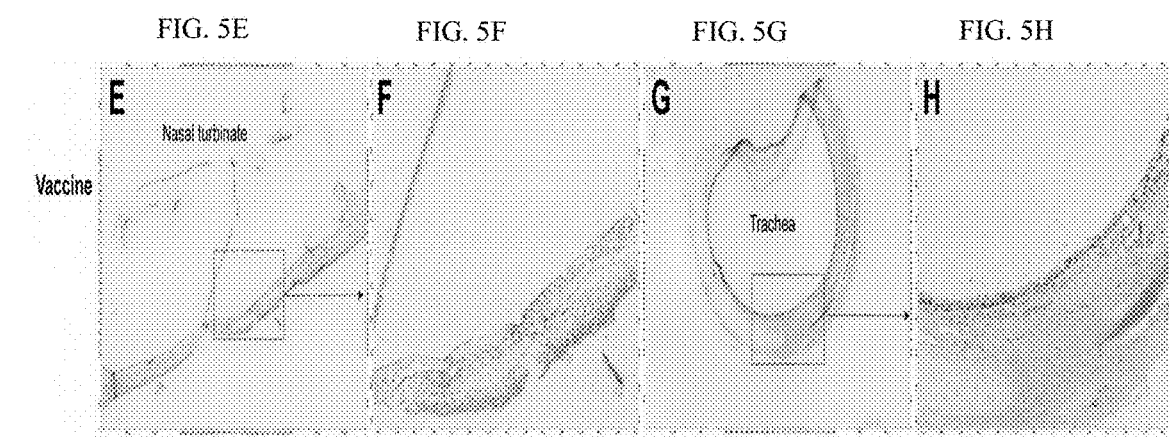
FIG. 5E is a photograph illustrating IDV RNA+ cells in nasal turbinate tissue in the vaccine group detected using in situ hybridization.
FIG. 5F is a magnified photograph of the area in the red box in FIG. 5E.
FIG. 5G is a photograph illustrating IDV RNA+ cells in tracheal tissue in the vaccine group detected using in situ hybridization.
FIG. 5H is a magnified photograph of the area in the red box of FIG. 5G.

To measure IDV infection, qRT-PCR and ISH were used to detect viral RNA in respiratory tract tissues collected from euthanized animals. Most IDV quantitative real-time PCR assays were designed based on the originally isolated PB1 sequence (4). Recently, Faccini S and colleagues improved this assay by targeting the primers and probe to the highly conserved segment of PB1 (21). Like PB1, NP is another conserved gene in influenza viruses including IDV, which has been a primary target for RT-PCR assay development. The new method developed in our study can serve as an alternative to the RT-PCR assay targeting the PB1 gene as published previously. In addition, there were other reasons make us develop the current NP gene based real-time PCR method. We did not have the PB1 standard used in the aforementioned assay, therefore, we developed a NP gene based real-time PCR method. High viral loads were readily detected using qRT-PCR in all the lung tissues of guinea pigs from both control groups, immunized with a sham vaccine and challenged with either D/OK or D/660 IDV. The mean viral RNA load in the D/OK control group (Mean±SD, 7.41±0.81, log 10) was significantly higher than the D/660 control group (5.52±2.52) (FIG. 3). In contrast, no IDV viral RNA was detected in any lung tissues from the vaccine groups, immunized with FluD-Vax and challenged with either D/OK or D/660 IDV (FIG. 3). To investigate whether IDV exists in peripheral blood in IDV infected animals, we conducted qRT-PCR and found that one animal was IDV positive in plasma (4.49E10 copies/ml). The animal with IDV positive plasma was infected with D/OK and had the highest viral load in lung tissues (8.5E10 copies/μg total RNA), indicating IDV from the respiratory tract can spread into peripheral blood if the IDV virus burden is very high. However, none of any other animals in the vaccine and control groups had detectable IDV RNA in plasma. To confirm qRT-PCR results, we detected viral RNA in respiratory tract tissues collected from euthanized animals using in situ hybridization (ISH). Consistent with the qRT-PCR results, ISH confirmed that all of the animals in the control groups were infected after IDV intranasal challenge, evident by the presence of abundant IDV vRNA positive cells in respiratory tract tissues, such as in lung (FIG. 4) and nasal turbinate and tracheal tissues (FIG. 5). The presence of IDV vRNA positive cells in nasal turbinate, septum, trachea, and lung tissues, further confirmed that IDV can infect both the upper and lower respiratory tract. Of note, IDV has a predisposition to infect the lungs (FIGS. 4 & 5). As shown in the FIGS. 4 & 5, both lineage representative IDVs infected bronchioles and alveoli of lung tissues with more vRNA+ cells found in bronchioles than alveoli. Representative images of FIG. 5 show that no IDV RNA+ cells (black silver grains in radioautographs, red arrows) were detected in any nasal turbinate (E & F, animal 1099) and tracheal tissues (G & H, animal 1099) of animals who received the FluD-Vax vaccine and were subsequently challenged with IDV D/OK or D/660. IDV RNA+ cells (black silver grains in radioautographs) were detected in nasal turbinate (A & B, animal 1084) and tracheal tissues (C & D, animal 1099) of control animals who received the sham vaccine and were subsequently challenged with IDV D/OK or D/660. Insets are magnified in images marked by shown arrows. As expected, we did not find IDV infected cells in the draining lymph node tissues of the lungs. Pan-cytokeratin immunohistochemical staining in combination with ISH confirmed that IDV infected cells were epithelial cells (FIG. 6). In FIG. 6, representative images show epithelial cells in lung tissues that were immunohistochemically stained as brown (Brown, in B, C, E, & F, animal 1084) with a pan-cytokeratin antibody and with IDV RNA underlaid of silver grains in radioautographs as cyan, yellow, or black color (red arrows) with different channel separation.

IDV Infection Caused Apoptosis in Lung Tissues

To determine whether IDV infection could cause programed cell death in lung tissues, we conducted TUNEL assays on lung tissues from all of the animals in the vaccine and control groups. We detected apoptotic cells in lung tissues on days 5 and 7 post IDV D/660 (FIG. 7C-F) and D/OK (FIG. 7I-L) infection in animals from the control groups. TUNEL-positive cells were mainly localized in the epithelial cells lining alveoli (FIGS. 7C, E, I & K, black arrows) and bronchioles (FIGS. 7D, F, H & L, black arrows within blue circles). However, TUNEL-positive cells were also detected in non-epithelial cells (FIG. 7, green arrows). In contrast, we did not observe TUNEL-positive cells in animals from the vaccine group (FIGS. 7A-B & G-H).

Discussion

The newly identified influenza D virus (DV) has been demonstrated to infect economically important domestic livestock, such as swine and cattle. IDV infection has been reported to be significantly associated with bovine respiratory disease complex (BRDC), which is the most economically significant disease affecting the U.S. cattle industry. While the level of infectivity and pathogenicity of IDV to humans remains to be determined, IDV has the potential to infect humans. IDV seroprevalence was estimated to be over 90% in individuals working closely with cattle. Moreover, IDV has a broad host range, which could enable IDV to gain virulence due to continual mutation, recombination, and evolution.

The development of a protective IDV vaccine is needed. However, the development of an effective vaccine is not simple, as a previous study showed that a chemical inactivated IDV vaccine did not provide sterilizing protection against even homologous virus challenge in bovine. As aforementioned, two genetically and serologically distinct lineages of IDV have been found to be co-circulating in cattle and equine. Therefore, This disclosure describes the development of a vaccine that could prevent infection by both lineages of IDV. Consensus sequence-based vaccine is a widely used approach to minimize the sequence diversity between a vaccine strain and circulating viruses, which can create an artificial sequence to "centralize" the immunogenicity of the vaccine antigen. In addition to the consensus sequence-based vaccine development approach, 'ancestor' and 'center of the tree' methods have also been applied to minimize the distance/mismatch of antigens between a vaccine and circulating viruses. As previously reported, when designing a consensus vaccine from the sequences of a symmetric phylogeny, these three methods generate very similar sequences. However, if the original sequences are from an asymmetric phylogeny, the consensus sequence will have a bias toward the dominant cluster of the input. In this study, a DNA vaccine encoding consensus IDV HEF protein (ConD-HEF) was designed and constructed. HEF surface protein was chosen for its key role in receptor binding, receptor destruction, and membrane fusion. Phylogenetic analysis showed that ConD-HEF is close to the center of the IDV phylogenetic tree with a slight bias toward the lineage represented by D/OK (FIG. 1). No further optimization was done to reduce this bias, because in natural infection, D/OK could generate relatively higher cross-reactive antibodies to D/660 represented lineage than D/660 to D/OK. In this study, 19 full-length IDV HEFs were used for the consensus vaccine design, including the 10 sequences that were previously analyzed for the identification of the two major circulating lineages (D/OK and D/660). For future vaccine design, including additional viral sequences, especially sequences that were isolated from different geographic locations, may further optimize the coverage of a consensus DNA IDV vaccine.

A previous study by this team established a guinea pigs/IDV model. With this model humoral immune responses elicited by the consensus HEF DNA vaccine (FluD-Vax) were evaluated. HI antibodies in blood against both D/OK and D/660 IDVs were detectable after the first immunization, were significantly boosted after the second immunization (>1:40), and peaked after the third immunization (FIGS. 2A and 2B). In this proof-of-concept study, in order to induce optimal humoral responses and achieve better protection, immunization was done 4 times. However, sterilizing protection may be induced by less than 4 immunizations and future studies are needed to determine the minimal number of immunizations to achieve sterilizing protection. A more robust HI antibody responses against D/OK than against D/660 (FIG. 2) was observed, which may be due to the intentional phylogenetic bias design of our consensus vaccine to D/OK. In silico comparative modeling of D/OK, D/660 and ConD HEF protein structures by SWISS-MODEL server as performed and found several amino acid substitutions in the receptor binding site of D/660 HEF (FIG. 2E). Although the consensus DNA vaccine elicited various levels of HI antibodies against D/OK and D/660, it protected all vaccinated animals from IDV D/OK and D/660 intranasal challenge, indicating vaccine-elicited immunity is potent enough to protect against both lineages of IDV infection (FIG. 3-5). In the FIG. 4 figures, IDV RNA+ cells (black silver grains in radioautographs) were detected in all of the lung tissues of animals who received the sham vaccine (control) and subsequently challenged intranasally with IDV D/OK (A-C, animal 1084) or D/660 (G-I, animal 1091), but were not detected in any lung tissues of animals who received the FluD-Vax vaccine and subsequently challenged with IDV D/OK (D-F, animal 1099) or D/660 (J-L, animal 1106). Red insets in the middle panel are magnified and shown in the left and right panels. In contrast, all animals in the control groups were infected after IDV challenge.

After D/OK and D/660 challenge, infected animals in the control groups had higher viral RNA loads in respiratory tissues at 5 dpi than 7 dpi by both q-RT-PCR and ISH assays, which is consistent with our previous study. IDV RNA$^+$ cells were detected in nasal turbinate, nasal septum, trachea, and lung tissues, indicating IDV can infect and replicate within the entire respiratory tract. Notably, within lung tissues, viral RNA$^+$ cells were detected in both alveoli and bronchioles, but more in bronchiolar cells. Using a combination of IHCS and ISH, it was shown that IDV solely infected epithelial cells. Although the exact protective mechanisms of the consensus vaccine against prevalent lineages of IDV infection was not fully investigated in this study, the results revealed that protection is correlated with HI antibody responses. One concern during IDV vaccine design is the potential for escape mutations that could minimize protection. However, the DNA vaccine expressing consensus IDV HEF in this study provided complete protection and prevented the occurrence of IDV escape mutations. However, IDV mutations can readily develop during IDV natural infection, thus a broad understanding of potentially mutated antigenic sites in IDV vaccine design is important.

The data suggested that the consensus HEF may be a good immunogen to protect against different lineages of IDV in large animals or even in humans. Further investigation is warranted to compare its efficacy with other vaccine modalities, such as inactivated and vectored vaccines.

Currently, the pathogenesis and resulting consequences of IDV infection in economically important animals are largely unknown. Apoptosis has been demonstrated to be an important anti-viral host defense to restrict influenza A and B virus replication. Paradoxically, apoptosis has also been implicated in inducing respiratory tissue damage during influenza virus infection. It was found for the first time that IDV infection induced TUNEL-positive apoptotic cells in epithelial cells lining alveoli (FIGS. 7C, E, I & K, black arrows) and bronchioles (FIGS. 7D, F, H & L, black arrows within blue dotted circles) in lung tissues of infected animals. Furthermore, we observed TUNEL-positive non-epithelial cells (FIG. 7, green arrows). Our results demonstrate that IDV infection causes apoptosis in lung tissues. Nevertheless, the dichotomy of protective and detrimental roles of apoptosis during IDV infection remains to be defined in future studies.

In summary, this study has demonstrated that a DNA vaccine expressing consensus IDV HEF can provide complete protection, which is correlated with HEF-specific antibody responses in a guinea pig model. Further, this study clearly demonstrated that IDV infects epithelial cells of both the upper and lower respiratory tract, including alveoli and bronchioles in lung tissues. More importantly, we found for the first time that IDV infection can induce programed cell death in lung tissues.

What is claimed is:

1. An immunogenic composition comprising a vector having an insert comprising a hemagglutinin esterase-fusion protein from the D/OK and D/660 strains of influenza D virus (IDV).

2. The immunogenic composition of claim 1, wherein said insert has a nucleotide sequence having at least 85% sequence homology with SEQ ID NO. 2.

3. The immunogenic composition of claim 1, further comprising at least one antigen from a pathogen other than IDV.

4. The immunogenic composition of claim 1, further comprising a veterinary acceptable carrier.

5. An immunogenic composition comprising a recombinant hemagglutinin esterase-fusion (HEF) protein from the D/OK and D/660 strains of IDV.

6. The immunogenic composition of claim 5, wherein said protein is expressed by a nucleotide sequence having at least 85% sequence homology with SEQ ID NO. 2.

7. The immunogenic composition of claim 5, wherein said protein has at least 85% sequence homology with SEQ ID. NO. 1.

8. The immunogenic composition of claim 5, further comprising at least one antigen from a pathogen other than IDV.

9. The immunogenic composition of claim 5, further comprising a veterinary acceptable carrier.

10. An immunogenic composition comprising a vector having an insert comprising a hemagglutinin esterase-fusion protein from influenza D virus (IDV), wherein said insert has a nucleotide sequence having at least 85% sequence homology with SEQ ID NO. 2.

11. The immunogenic composition of claim 10, further comprising at least one antigen from a pathogen other than IDV.

12. An immunogenic composition comprising a recombinant hemagglutinin esterase-fusion (FIEF) protein from influenza D virus (IDV) wherein said protein is expressed by a nucleotide sequence having at least 85% sequence homology with SEQ ID NO. 2.

13. The immunogenic composition of claim 12, further comprising at least one antigen from a pathogen other than IDV.

14. A method of reducing the incidence or severity of IDV infection in an animal comprising the steps of:
   administering an effective amount of an immunogenic composition to an animal in need thereof, wherein said immunogenic composition is selected from the group consisting of the immunogenic composition of claim 1, the immunogenic composition of claim 5, the immunogenic composition of claim 10, the immunogenic composition of claim 12, and any combination thereof.

15. The method of claim 14, wherein said administration is delivered via injection, intranasally, or orally.

16. The method of claim 14, wherein said administration is performed more than one time.

17. The method of claim 14, further comprising the step of administering an antigen from another pathogen other than IDV.

18. The method of claim 17, wherein said antigen from another pathogen other than IDV is combined with said immunogenic composition.

19. The method of claim 14, wherein said animal in need thereof is selected from the group consisting of cows and pigs.

20. The method of claim 14, wherein said reducing the incidence or severity of clinical signs of IDV infection is in comparison to an animal that has not received an administration of said immunogenic composition.

* * * * *

SEQUENCE LISTING

<160> NUMBER OF SEQ ID NOS: 9

<210> SEQ ID NO 1
<211> LENGTH: 664
<212> TYPE: PRT
<213> ORGANISM: Artificial Sequence
<220> FEATURE:
<223> OTHER INFORMATION: consensus sequence of hemagglutinin esterase
      fusion protein of IDV

<400> SEQUENCE: 1

Met Phe Leu Leu Leu Ala Thr Ile Thr Ala Ile Thr Ala Cys Gln Ala
1               5                   10                  15

Glu Arg Glu Leu Ile Cys Ile Val Gln Arg Val Asn Glu Ser Phe Ser
            20                  25                  30

Leu His Ser Gly Phe Gly Gly Asn Val Tyr Ser Met Lys Thr Glu Pro
        35                  40                  45

Met Thr Gly Phe Thr Asn Val Thr Lys Gly Ala Ser Val Ile Asn Gln
    50                  55                  60

Lys Asp Trp Ile Gly Phe Gly Asp Ser Arg Thr Asp Leu Thr Asn Asp
65                  70                  75                  80

Gln Phe Pro Ala Ser Ser Asp Val Pro Leu Ala Val Ala Lys Lys Phe
                85                  90                  95

Arg Ser Leu Ser Gly Ala Ser Leu Met Leu Ser Ala Phe Gly Pro Pro
            100                 105                 110

Gly Lys Val Asp Tyr Leu Tyr Gln Gly Cys Gly Lys Glu Lys Val Phe
        115                 120                 125

Tyr Glu Gly Val Asn Trp Ser Pro Glu Ala Gly Ile Asp Cys Phe Gly
    130                 135                 140

Ser Asn Trp Thr Gln Thr Lys Lys Asp Phe Tyr Ser Arg Ile Tyr Glu
145                 150                 155                 160

Ala Ala Arg Gly Ser Thr Cys Met Thr Leu Val Asn Ser Leu Asp Thr
                165                 170                 175

Lys Ile Ser Ser Thr Thr Ala Thr Ala Gly Thr Ala Ser Ser Cys Ser
            180                 185                 190

Ser Ser Trp Met Lys Ser Pro Leu Trp Tyr Ala Glu Ser Ser Val Asn
        195                 200                 205

Pro Gly Ala Lys Pro Gln Val Cys Gly Thr Glu Gln Ser Ala Thr Phe
    210                 215                 220

Thr Leu Pro Thr Ser Phe Gly Ile Tyr Lys Cys Asn Lys His Val Val
225                 230                 235                 240

Gln Leu Cys Tyr Phe Val Tyr Glu Asn Lys Thr Thr Phe Asn Thr Phe
                245                 250                 255

Gly Cys Gly Asp Tyr Tyr Gln Asn Tyr Tyr Asp Gly Asn Gly Asn Leu
            260                 265                 270

Ile Gly Gly Met Asp Asn Arg Val Ala Ala Tyr Arg Gly Ile Ala Asn
        275                 280                 285

Ala Gly Val Lys Ile Glu Cys Pro Ser Lys Ile Leu Asn Pro Gly Thr
    290                 295                 300

Tyr Ser Ile Arg Ser Thr Pro Arg Phe Leu Leu Val Pro Lys Arg Ser
305                 310                 315                 320

Tyr Cys Phe Asp Thr Asp Gly Gly Tyr Pro Ile Gln Val Val Gln Ser
                325                 330                 335

Glu Trp Ser Ala Ser Arg Arg Ser Asp Asn Ala Thr Glu Glu Ala Cys
            340                 345                 350

| | | | | | | | | | | | |
|---|---|---|---|---|---|---|---|---|---|---|---|
|Leu|Gln|Thr|Glu|Gly|Cys|Ile|Phe|Ile|Lys|Lys|Thr|Thr|Pro|Tyr|Val|
| | |355| | | |360| | | |365| |

Leu Gln Thr Glu Gly Cys Ile Phe Ile Lys Lys Thr Thr Pro Tyr Val
          355                    360              365

Gly Glu Ala Asp Asp Asn His Gly Asp Ile Glu Met Arg Gln Leu Leu
370                   375               380

Ser Gly Leu Gly Asn Asn Asp Thr Val Cys Val Ser Gln Ser Gly Tyr
385                390             395               400

Thr Lys Gly Glu Thr Pro Phe Val Lys Asp Tyr Leu Ser Pro Pro Lys
          405                  410              415

Tyr Gly Arg Cys Gln Leu Lys Thr Asp Ser Gly Arg Ile Pro Thr Leu
          420                  425              430

Pro Ser Gly Leu Ile Ile Pro Gln Ala Gly Thr Asp Ser Leu Met Arg
          435                  440              445

Thr Leu Thr Pro Ala Thr Arg Ile Phe Gly Ile Asp Asp Leu Ile Phe
    450                  455              460

Gly Leu Leu Phe Val Gly Phe Val Ala Gly Val Ala Gly Gly Tyr
465                470             475               480

Phe Trp Gly Arg Ser Asn Gly Gly Gly Gly Ala Ser Val Ser Ser
          485                  490              495

Thr Gln Ala Gly Phe Asp Lys Ile Gly Lys Asp Ile Gln Gln Leu Arg
          500                  505              510

Asn Asp Thr Asn Ala Ala Ile Glu Gly Phe Asn Gly Arg Ile Ala His
          515                  520              525

Asp Glu Gln Ala Ile Lys Asn Leu Ala Lys Glu Ile Glu Asp Ala Arg
          530                  535              540

Ala Glu Ala Leu Val Gly Glu Leu Gly Ile Ile Arg Ser Leu Ile Val
545                550             555               560

Ala Asn Ile Ser Met Asn Leu Lys Glu Ser Leu Tyr Glu Leu Ala Asn
          565                  570              575

Gln Ile Thr Lys Arg Gly Gly Gly Ile Ala Gln Glu Ala Gly Pro Gly
          580                  585              590

Cys Trp Tyr Val Asp Ser Glu Asn Cys Asp Ala Ser Cys Lys Glu Tyr
          595                  600              605

Ile Phe Asn Phe Asn Gly Ser Ala Thr Val Pro Thr Leu Arg Pro Val
610                615             620

Asp Thr Lys Val Val Ile Thr Ser Asp Pro Tyr Tyr Leu Gly Ser Thr
625                630             635               640

Ile Ala Leu Cys Leu Leu Gly Leu Val Ala Ile Ala Ala Ser Val Gly
          645                  650              655

Val Ile Trp Ile Cys Cys Lys Lys
          660

<210> SEQ ID NO 2
<211> LENGTH: 1995
<212> TYPE: DNA
<213> ORGANISM: Artificial Sequence
<220> FEATURE:
<223> OTHER INFORMATION: Consensus nucleotide sequence of hemagglutinin
    esterase fusion protein of IDV

<400> SEQUENCE: 2

```
atgttcctgc tgctggccac catcaccgcc atcaccgcct gccaggccga gagggagctg      60
atctgcatcg tgcagagggt gaacgagagc ttcagcctgc acagcggctt cggcggcaac     120
gtgtacagca tgaagaccga gcccatgacc ggcttcacca acgtgaccaa gggcgccagc     180
gtgatcaacc agaaggactg gatcggcttc ggcgacagca ggaccgacct gaccaacgac     240
```

```
cagttccccg ccagcagcga cgtgcccctg gccgtggcca agaagttcag gagcctgagc    300
ggcgccagcc tgatgctgag cgccttcggc ccccccggca aggtggacta cctgtaccag    360
ggctgcggca aggagaaggt gttctacgag ggcgtgaact ggagccccga ggccggcatc    420
gactgcttcg gcagcaactg gacccagacc aagaaggact tctacagcag gatctacgag    480
gccgccaggg gcagcacctg catgaccctg gtgaacagcc tggacaccaa gatcagcagc    540
accaccgcca ccgccggcac cgccagcagc tgcagcagca gctggatgaa gagcccctg     600 tggtacgccg agagcagcgt gaaccccggc gccaagcccc aggtgtgcgg caccgagcag    660
agcgccacct tcaccctgcc caccagcttc ggcatctaca agtgcaacaa gcacgtggtg    720
cagctgtgct acttcgtgta cgagaacaag accaccttca acaccttcgg ctgcggcgac    780
tactaccaga actactacga cggcaacggc aacctgatcg gcggcatgga caacagggtg    840
gccgcctaca ggggcatcgc caacgccggc gtgaagatcg agtgccccag caagatcctg    900
aaccccggca cctacagcat caggagcacc cccaggttcc tgctggtgcc aagaggagc    960 tactgcttcg acaccgacgg cggctacccc atccaggtgg tgcagagcga gtggagcgcc   1020
agcaggagga gcgacaacgc caccgaggag gcctgcctgc agaccgaggg ctgcatcttc   1080
atcaagaaga ccacccccta cgtgggcgag gccgacgaca ccacggcga catcgagatg    1140 aggcagctgc tgagcggcct gggcaacaac gacaccgtgt gcgtgagcca gagcggctac   1200
accaagggcg agacccccTT cgtgaaggac tacctgagcc cccccaagta cggcaggtgc   1260
cagctgaaga ccgacagcgg caggatacccc accctgccca gcggcctgat catcccccag   1320
gccggcaccg acagcctgat gaggaccctg accccgccca ccaggatctt cggcatcgac   1380
gacctgatct tcggcctgct gttcgtgggc ttcgtggccg gcggcgtggc cggcggctac   1440
ttctggggca ggagcaacgg cggcggcggc ggcgccagcg tgagcagcac ccaggccggc   1500
ttcgacaaga tcggcaagga catccagcag ctgaggaacg acaccaacgc cgccatcgag   1560
ggcttcaacg gcaggatcgc ccacgacgag caggccatca agaacctggc caaggagatc   1620
gaggacgcca gggccgaggc cctggtgggc gagctgggca tcatcaggag cctgatcgtg   1680
gccaacatca gcatgaacct gaaggagagc ctgtacgagc tggccaacca gatcaccaag   1740
aggggcggcg gcatcgccca ggaggccggc cccggctgct ggtacgtgga cagcgagaac   1800
tgcgacgcca gctgcaagga gtacatcttc aacttcaacg gcagcgccac cgtgcccacc   1860
ctgaggcccg tggacaccaa ggtggtgatc accagcgacc cctactacct gggcagcacc   1920
atcgccctgt gcctgctggg cctggtggcc atcgccgcca gcgtgggcgt gatctggatc   1980
tgctgcaaga agtag                                                   1995
```

<210> SEQ ID NO 3
<211> LENGTH: 20
<212> TYPE: DNA
<213> ORGANISM: Artificial Sequence
<220> FEATURE:
<223> OTHER INFORMATION: artificial primer for IDV

<400> SEQUENCE: 3
aagcgacgtt ccaagaactg                                               20

<210> SEQ ID NO 4
<211> LENGTH: 20
<212> TYPE: DNA
<213> ORGANISM: Artificial Sequence
<220> FEATURE:
<223> OTHER INFORMATION: artificial primer for IDV

```
<400> SEQUENCE: 4
gggactgcaa cagaaccatc                                               20

<210> SEQ ID NO 5
<211> LENGTH: 21
<212> TYPE: DNA
<213> ORGANISM: Artificial Sequence
<220> FEATURE:
<223> OTHER INFORMATION: artificial primer for IDV

<400> SEQUENCE: 5
tgctccggca ccttgccttc c                                             21

<210> SEQ ID NO 6
<211> LENGTH: 46
<212> TYPE: DNA
<213> ORGANISM: Artificial Sequence
<220> FEATURE:
<223> OTHER INFORMATION: artificial primer for IDV

<400> SEQUENCE: 6
aacgtgtaat acgactcact atagggaggg gcttcgttga tgttgt                  46

<210> SEQ ID NO 7
<211> LENGTH: 44
<212> TYPE: DNA
<213> ORGANISM: Artificial Sequence
<220> FEATURE:
<223> OTHER INFORMATION: artificial primer for IDV

<400> SEQUENCE: 7
aactggattt aggtgacact atagaagatc cttgttgctg gcgt                    44

<210> SEQ ID NO 8
<211> LENGTH: 46
<212> TYPE: DNA
<213> ORGANISM: Artificial Sequence
<220> FEATURE:
<223> OTHER INFORMATION: artificial primer for IDV

<400> SEQUENCE: 8
aacgtgtaat acgactcact atagggtggc aagcaaaaag aacggg                  46

<210> SEQ ID NO 9
<211> LENGTH: 45
<212> TYPE: DNA
<213> ORGANISM: Artificial Sequence
<220> FEATURE:
<223> OTHER INFORMATION: artificial primer for IDV

<400> SEQUENCE: 9
aactggattt aggtgacact atagacctct tttcttgggc tggga                   45
```